US012796920B2

(12) United States Patent
Wang et al.

(10) Patent No.: US 12,796,920 B2
(45) Date of Patent: Nov. 17, 2026

(54) METHOD AND SYSTEM FOR MEASURING LESION FEATURES OF HYPERTENSIVE RETINOPATHY

(71) Applicant: SHENZHEN SIBRIGHT TECHNOLOGY CO., LTD., Shenzhen (CN)

(72) Inventors: Juan Wang, Shenzhen (CN); Xiaoming Duan, Shenzhen (CN); Jianghuai Xiang, Shenzhen (CN); Suping Chen, Shenzhen (CN); Bin Xia, Shenzhen (CN)

(73) Assignee: SHENZHEN SIBRIGHT TECHNOLOGY CO., LTD., Shenzhen (CN)

( * ) Notice: Subject to any disclaimer, the term of this patent is extended or adjusted under 35 U.S.C. 154(b) by 260 days.

(21) Appl. No.: 18/259,391

(22) PCT Filed: Apr. 29, 2021

(86) PCT No.: PCT/CN2021/091226

§ 371 (c)(1),
(2) Date: Jun. 26, 2023

(87) PCT Pub. No.: WO2022/142030

PCT Pub. Date: Jul. 7, 2022

(65) Prior Publication Data

US 2024/0074658 A1 Mar. 7, 2024

(30) Foreign Application Priority Data

Dec. 28, 2020 (CN) ........................ 202011585139.9

(51) Int. Cl.
*G06T 7/11* (2017.01)
*A61B 3/00* (2006.01)
(Continued)

(52) U.S. Cl.
CPC .............. *A61B 3/12* (2013.01); *A61B 3/0025* (2013.01); *G06T 7/0012* (2013.01); *G06T 7/11* (2017.01);
(Continued)

(58) Field of Classification Search
CPC ........... A61B 3/12; A61B 3/0025; A61B 3/14; A61B 5/0033; A61B 5/02; A61B 5/02007;
(Continued)

(56) References Cited

U.S. PATENT DOCUMENTS

2012/0257164 A1* 10/2012 Zee .......................... A61B 3/12 351/246
2016/0166141 A1 6/2016 Kanagasingam et al.
2020/0349710 A1* 11/2020 Paschalakis ......... A61B 3/0025

FOREIGN PATENT DOCUMENTS

CN 107292887 A 10/2017
CN 110197493 A 9/2019
(Continued)

OTHER PUBLICATIONS

S. Irshad and M. U. Akram, "Classification of retinal vessels into arteries and veins for detection of hypertensive retinopathy," 2014 Cairo International Biomedical Engineering Conference (CIBEC), Giza, Egypt, 2014, pp. 133-136, doi: 10.1109/CIBEC.2014.7020937 (Year: 2014).*
(Continued)

*Primary Examiner* — Sharrief I Broome
*Assistant Examiner* — K Muhammad
(74) *Attorney, Agent, or Firm* — AVEK IP, LLC

(57) ABSTRACT

Some embodiments of the disclosure provide a method for measuring lesion features of hypertensive retinopathy. In some examples, the method includes: acquiring a fundus image (s110); identifying an optic disc region of the fundus
(Continued)

image and dividing the fundus image into at least three regions including a first region (c1), a second region (c2), and a third region (c3) on the basis of the optic disc region (b) (s120); performing artery and vein segmentation on the fundus image by a deep learning-based arteriovenous segmentation model to obtain the arteriovenous segmentation result (s130), the arteriovenous vessel annotation results including an artery annotation result (e1), a vein annotation result (e2), and a small vessel annotation result (e3); and measuring lesion features in the fundus image on the basis of the three regions (c1, c2, c3) and the arteriovenous segmentation result (s140).

13 Claims, 12 Drawing Sheets

(51) Int. Cl.
*A61B 3/12* (2006.01)
*G06T 7/00* (2017.01)

(52) U.S. Cl.
CPC ............... *G06T 2207/30041* (2013.01); *G06T 2207/30101* (2013.01)

(58) Field of Classification Search
CPC ....... A61B 5/1075; G06T 7/0012; G06T 7/11; G06T 2207/30041; G06T 2207/30101; G06T 2207/20084; G06T 7/12; G06T 2207/20081; G06T 2207/30204
See application file for complete search history.

(56) References Cited

FOREIGN PATENT DOCUMENTS

| | | | | | |
|---|---|---|---|---|---|
| CN | 111047613 | A | | 4/2020 | |
| CN | 111222361 | A | | 6/2020 | |
| CN | 111340789 | A | | 6/2020 | |
| CN | 111435612 | A | | 7/2020 | |
| CN | 111681242 | A | | 9/2020 | |
| CN | 111681276 | A | * | 9/2020 | ........... G06T 7/0012 |
| CN | 111932535 | A | | 11/2020 | |

OTHER PUBLICATIONS

Badawi SA, Fraz MM. Multiloss Function Based Deep Convolutional Neural Network for Segmentation of Retinal Vasculature into Arterioles and Venules. Biomed Res Int. Apr. 14, 2019; vol. 2019, pp. 1-17; 2019:4747230. doi: 10.1155/2019/4747230. PMID: 31111055; PMCID: PMC6487175 (Year: 2019).*

Joshi VS, Reinhardt JM, Garvin MK, Abramoff MD. Automated method for identification and artery-venous classification of vessel trees in retinal vessel networks. PLoS One. Feb. 12, 2014;9(2):e88061. doi: 10.1371/journal.pone.0088061. PMID: 24533066; PMCID: PMC3922768. (Year: 2014).*

International Search Report for PCT/CN2021/091226 issued by CNIPA (China National Intellectual Property Administration) on Sep. 28, 2021.

* cited by examiner

METHOD AND SYSTEM FOR MEASURING LESION FEATURES OF HYPERTENSIVE RETINOPATHY

CROSS REFERENCE TO RELATED APPLICATIONS

This application is the United State national stage entry under 37 U.S.C. 371 of PCT/CN2021/091226, filed on Apr. 29, 2021, which claims priority to Chinese application number 202011585139.9, filed on Dec. 28, 2020, the disclosure of which are incorporated by reference herein in their entireties.

FIELD OF THE DISCLOSURE

The disclosure relates generally to the field of medical systems and methods. More specifically, the disclosure relates to methods and systems for measuring lesion features of hypertensive retinopathy.

BACKGROUND

The number of hypertensive patients in China is increasing year by year, with hundreds of millions of people suffering from hypertension, and it is worrying that the age at which hypertension occurs is becoming younger. Hypertension is easy to cause complications such as myocardial infarction, renal failure, cerebral hemorrhage, cerebral infarction and uremia, which are life-threatening. Therefore, early identification and intervention of hypertension is of great significance.

Clinically, hypertension may be determined by measuring blood pressure. However, measurement of blood pressure generally is not able to assess the patient's recent or long-term hypertension. Presently, the severity of hypertension in patients may be assessed by observing vascular changes in the fundus of the eye to obtain lesion features (e.g., arteriovenous cross-indentation features, arteriolar local stenosis features or arteriolar general stenosis features) of hypertensive retinopathy that may reflect hypertension. In general, the arteriolar local stenosis features may reflect the patient's recent increase in blood pressure, and the arteriovenous cross-indentation features and the arteriolar general stenosis features may reflect the patient's long-term sustained increase in blood pressure. In this case, other features (e.g., retinal hemorrhage or microangioma) may be incorporated to assist an ophthalmologist to identify the conditions of hypertension. In current methods, fundus images are usually obtained using fundus photography to facilitate the ophthalmologist to observe and measure the lesion features of hypertensive retinopathy. However, the artificial measurement of lesion features is time consuming and has certain subjectivity.

SUMMARY

The following presents a simplified summary of the invention in order to provide a basic understanding of some aspects of the invention. This summary is not an extensive overview of the invention. It is not intended to identify critical elements or to delineate the scope of the invention. Its sole purpose is to present some concepts of the invention in a simplified form as a prelude to the more detailed description that is presented elsewhere.

In some embodiments, a first aspect of the present disclosure provides a method for measuring lesion features of hypertensive retinopathy, including: acquiring a fundus image; identifying an optic disc region of the fundus image and dividing the fundus image into at least three regions including a first region, a second region, and a third region based on the optic disc region; performing artery and vein segmentation on the fundus image by an arteriovenous segmentation model based on a training fundus image, an arteriovenous vessel annotation result, and deep learning to acquire an arteriovenous segmentation result. Here, the arteriovenous segmentation results include an artery segmentation result and a vein segmentation result; and measuring the lesion features of the hypertensive retinopathy in the fundus image based on the three regions and the arteriovenous segmentation results, the lesion features include at least one of arteriovenous cross-indentation features, arteriolar local stenosis features, and arteriolar general stenosis features, the arteriovenous vessel annotation results include an artery annotation result and a vein annotation result formed by annotating the boundary of a vessel with a vessel diameter greater than a pre-set vessel diameter in the training fundus image and a small vessel annotation result formed by annotating the direction of a vessel with the diameter not greater than the pre-set vessel diameter, when a loss function is calculated, a weight of a region corresponding to the small vessel annotation result is adjusted based on the small vessel annotation result. In this case, the fundus image is partitioned based on the optic disc region to obtain at least three regions, artery and vein segmentation is performed on the fundus image through a depth learning-based arteriovenous segmentation model to obtain an arteriovenous segmentation result, and the lesion features of the hypertensive retinopathy in the fundus image are automatically measured based on the three regions and the arteriovenous segmentation results. Thus, the lesion features of hypertensive retinopathy may be measured efficiently and objectively.

In addition, in the measurement method according to the first aspect of the present disclosure, optionally, the first region is a region of a first circle formed by taking a circle center of a circumscribed circle of the optic disc region as the center and a first pre-set multiple of a diameter of the circumscribed circle as the diameter; the second region is a region from the edge of the first region to a second circle formed by taking the circle center as the center and a second pre-set multiple of the diameter of the circumscribed circle as the diameter; and the third region is a region from the edge of the second region to a third circle formed by taking the circle center as the center and a third pre-set multiple of the diameter of the circumscribed circle. Here, $v1<v2<v3$, v1 represents a first pre-set multiple; v2 represents a second pre-set multiple, and v3 represents a third pre-set multiple. Thus, three regions may be acquired based on the optic disc region.

In addition, in the measurement method according to the first aspect of the present disclosure, optionally, if the arteriovenous cross-indentation features are measured, the arteriovenous segmentation results of a fundus region except the first region and the second region are thinned to acquire a first vessel skeleton including a plurality of skeleton pixel points taken as first measurement pixel points and to acquire the number of skeleton pixel points within a pre-set range of each of the first measurement pixel points as a first adjacent point number, pixel points in the arteriovenous segmentation results corresponding to the first measurement pixel points of which the number of first adjacent points is greater than a first pre-set number are taken as arteriovenous cross positions, arteriovenous cross-indentation features are measured based on a ratio of proximal and distal vessel diameters in the arteriovenous segmentation results along the direction of extension of the vein segmentation result and on each of both sides of the arteriovenous cross position. Thereby, it is able to measure the arteriovenous cross-indentation features based on the arteriovenous cross position.

In addition, in the measurement method according to the first aspect of the present disclosure, optionally, if the arteriolar local stenosis features are measured, the artery segmentation result is thinned to acquire a second vessel skeleton including a plurality of skeleton pixel points taken as second measurement pixel points, the number of skeleton pixel points within a pre-set range of each of the second measurement pixel points are acquired as the second adjacent point number, the second measurement pixel points with the number of the second adjacent points being greater than the second pre-set number are deleted to obtain a plurality of vessel segments, the arteriolar local stenosis features are measured based on a ratio of a minimum vessel diameter to a maximum vessel diameter of each vessel segment. Thus, the arteriolar local stenosis features may be measured.

In addition, in the measurement method according to the first aspect of the present disclosure, optionally, if the arteriolar general stenosis features are measured, an artery vessel segment and a vein vessel segment in the third region in the arteriovenous segmentation result are acquired, an arteriole-to-venule ratio is obtained based on the artery vessel segment, the vein vessel segment and a pre-set formula to measure the arteriolar general stenosis features, the pre-set formula is a correction formula of Knudtson. Thus, the arteriolar general stenosis features may be measured based on the artery vessel segment and the vein vessel segment in the third region.

In addition, in the measurement method according to the first aspect of the present disclosure, optionally, during the measurement of the arteriovenous cross-indentation features, the artery segmentation results are expanded such that the expanded artery segmentation results intersect the vein segmentation results to determine the arteriovenous cross positions. Thus, the arteriovenous cross positions may be obtained more accurately.

In addition, in the measurement method according to the first aspect of the present disclosure, optionally, if the vein segmentation result is discontinuous at the arteriovenous cross position in the arteriovenous segmentation result, the proximal end of each side is a skeleton pixel point on the first vessel skeleton of the vein segmentation result which is closest to the arteriovenous cross position; if the vein segmentation result is continuous at the arteriovenous cross position in the arteriovenous segmentation result, the proximal end of each side is the arteriovenous cross position; and the distal end of each side is a skeleton pixel point on the first vessel skeleton of the vein segmentation result to which a distance from the arteriovenous cross position is a first pre-set distance. Thus, the proximal and distal ends of both sides of the vein segmentation result may be determined based on the arteriovenous cross positions.

In addition, in the measurement method according to the first aspect of the present disclosure, optionally, the first pre-set distance is 2 to 4 times the maximum vessel diameter, and the first pre-set number is 3. Thus, the first pre-set distance and the first predetermined number may be acquired.

In addition, in the measurement method according to the first aspect of the present disclosure, optionally, the second pre-set number is 2, v1 is 1, v2 is 2, v3 is 3, and the pre-set vessel diameter is 50 μm. Thus, the second pre-set number, the first pre-set multiple, the second pre-set multiple, the third pre-set multiple and the pre-set vessel diameter may be acquired.

In addition, in the measurement method according to the first aspect of the present disclosure, optionally, measuring a vessel diameter includes performing resolution enhancement on the arteriovenous segmentation result according to a pre-set multiple to generate an enhanced arteriovenous segmentation result; extracting a vessel skeleton in the enhanced arteriovenous segmentation result and fitting the vessel skeleton to obtain a vessel diameter measurement direction of a continuous vessel skeleton and third measurement pixel points, the third measurement pixel points are a plurality of pixel points on the continuous vessel skeleton, and the vessel diameter measurement direction is perpendicular to a tangent line of the continuous vessel skeleton at the third measurement pixel point; using an interpolation algorithm to generate a vessel contour corresponding to the third measurement pixel point based on the enhanced arteriovenous segmentation result, the third measurement pixel points, the vessel diameter measurement direction of the third measurement pixel points, and a pre-set accuracy; calculating a vessel diameter corresponding to the third measurement pixel point based on the number of vessel pixel points in the vessel contour corresponding to the third measurement pixel point, the pre-set multiple and the pre-set accuracy, a vessel diameter 1 corresponding to the third measurement pixel point satisfies: $l=n\times s/e$. Here, n is the number of vessel pixel points in the vessel contour corresponding to the third measurement pixel point, s is the pre-set accuracy, and e is the pre-set multiple. In this case, the resolution of the vessel in the fundus image may be increased and more pixels are used to measure the vessel diameter. Thus, it is able to perform automatic super-resolution measurement of the vessel diameter and improve the measurement accuracy of the vessel diameter.

In addition, in the measurement method according to the first aspect of the present disclosure, optionally, the weight is adjusted to be zero. In this case, it is able to exclude the contribution to the loss function of the small vessel annotation result and its vicinity with only the direction marked. Thus, it is able to avoid the influence of the small vessel annotation result having low accuracy in the arteriovenous segmentation on the arteriovenous segmentation model.

A second aspect of the present disclosure provides a system for measuring lesion features of hypertensive retinopathy, including: an acquisition module, used for acquiring a fundus image; a partitioning module, used for receiving the fundus image, identifying an optic disc region of the fundus image and dividing the fundus image into at least three regions including a first region, a second region, and a third region based on the optic disc region; a segmentation module, used for performing artery and vein segmentation on the fundus image by an arteriovenous segmentation model based on a training fundus image, an arteriovenous vessel annotation result, and deep learning to acquire an arteriovenous segmentation result. The arteriovenous segmentation results include an artery segmentation result and a vein segmentation result; and a measurement module, used for measuring the lesion features of the hypertensive retinopathy in the fundus image based on the three regions and the arteriovenous segmentation results, the lesion features include at least one of arteriovenous cross-indentation features, arteriolar local stenosis features, and arteriolar general stenosis features, the arteriovenous vessel annotation results include an artery annotation result and a vein annotation result formed by annotating the boundary of a vessel with a vessel diameter greater than a pre-set vessel diameter in the training fundus image and a small vessel annotation result formed by annotating the direction of a vessel not greater than the pre-set vessel diameter, when a loss function is calculated, a weight of a region corresponding to the small vessel annotation result is adjusted based on the small vessel annotation result. In this case, the fundus image is partitioned based on the optic disc region to acquire three regions, artery and vein segmentation is performed on the fundus image through a depth learning-based arteriovenous segmentation model to obtain an arteriovenous segmentation result, and the lesion features of the hypertensive retinopathy in the fundus image are automatically measured based on the three regions and the arteriovenous segmentation results. Thus, the lesion features of hypertensive retinopathy may be measured efficiently and objectively.

In accordance with the present disclosure, it provides a method and system for measuring lesion features of hypertensive retinopathy that may efficiently and objectively measure the lesion features of hypertensive retinopathy.

BRIEF DESCRIPTION OF THE DRAWINGS

Illustrative embodiments of the present disclosure are described in detail below with reference to the attached drawing figures.

DETAILED DESCRIPTION

The following describes some non-limiting exemplary embodiments of the invention with reference to the accompanying drawings. The described embodiments are merely a part rather than all of the embodiments of the invention. All other embodiments obtained by a person of ordinary skill in the art based on the embodiments of the disclosure shall fall within the scope of the disclosure.

Figure 1:
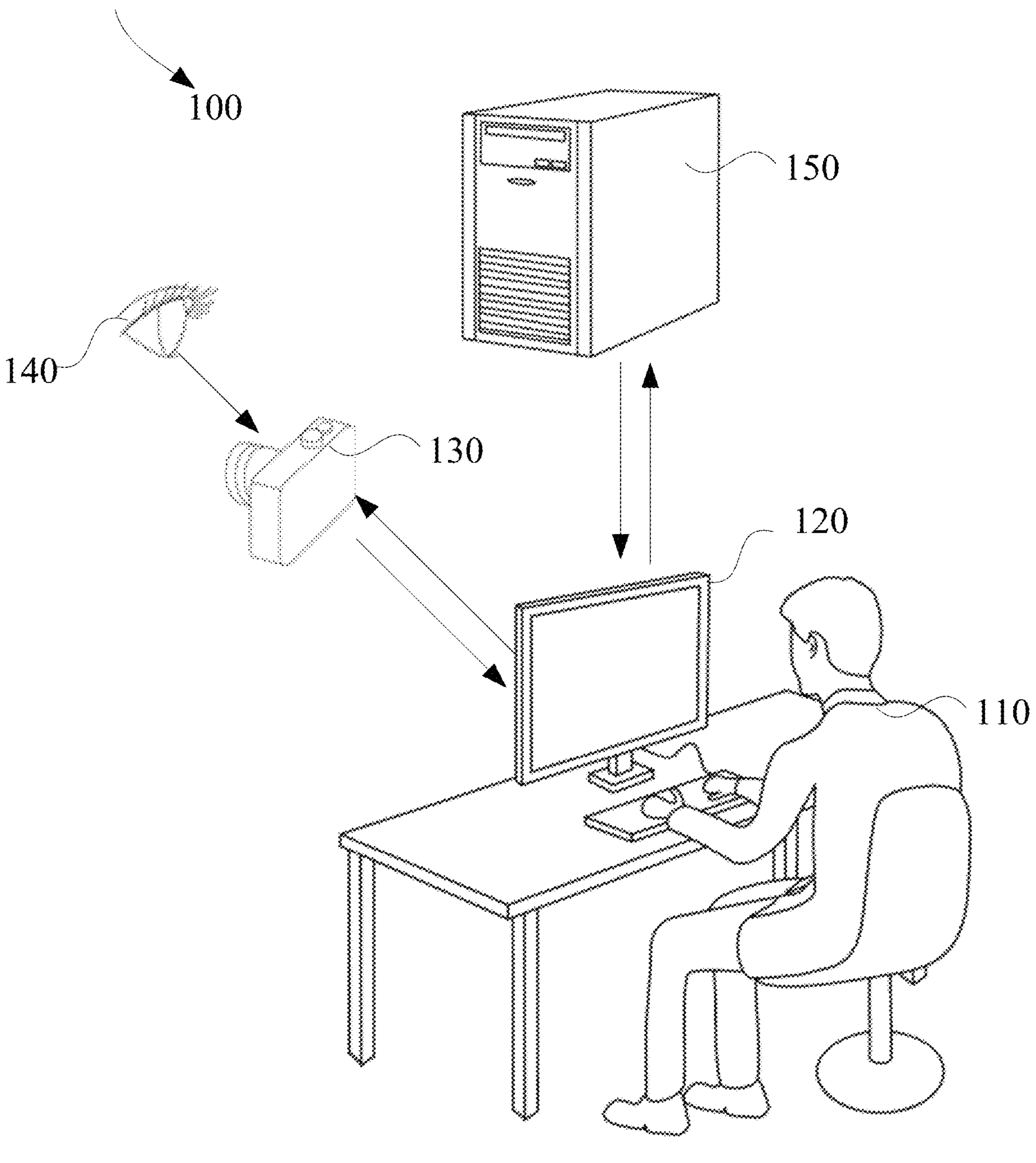
FIG. 1 is a schematic diagram showing an application scenario of a lesion feature measurement method of hypertensive retinopathy according to an embodiment of the disclosure.

FIG. 1 is a schematic diagram showing an application scenario of a lesion feature measurement method of hypertensive retinopathy according to an embodiment of the disclosure. In some examples, the present disclosure relates to a method for measuring lesion features of hypertensive retinopathy (sometimes referred to simply as a measurement method), which may be applied in an application scenario 100 as shown in FIG. 1. In the application scenario 100, an operator 110 may collect a fundus image of a human eye 140 by controlling a collecting device 130 connected to the terminal 120. After the collecting device 130 completes the fundus image acquisition, a terminal 120 may submit the fundus image to a server 150 via a computer network. The server 150 executes computer program instructions to implement a measurement method that may obtain the lesion features (described later, sometimes simply referred to as lesion features) of hypertensive retinopathy in the fundus image and return the lesion features to the terminal 120. In some examples, the terminal 120 may display whether the lesion features are present or not. In other examples, the lesion features may be stored as intermediate results in the terminal 120 or a memory of the server 150.

In some examples, the operator 110 may be a physician with expertise in measuring the lesion features in fundus images. In other examples, the operator 110 may be an ordinary person familiar with how to automatically measure the lesion features by operating the terminal 120. The terminal 120 may include, but is not limited to, a notebook computer, a tablet computer, or a desktop computer, etc. In some examples, the terminal 120 may be a dedicated device that measures the lesion features including a processor, a memory, a display screen, and a collecting device 130. The collecting device 130 may include, but is not limited to, a camera or the like. The camera may be, for example, a color fundus camera. In some examples, the collecting device 130 may be connected to or integrated into the terminal 120 via a serial port.

In some examples, the fundus of the human eye 140 refers to the tissues in the posterior portion of the eyeball, which may include the inner membrane, retina, macula, and vessels (retinal arteries and veins) of the eyeball. In some examples, the lesion features may be identified by monitoring vascular changes in the fundus of the human eye 140. In some examples, the server 150 may include one or more processors and one or more memories. The processor may include a central processing unit, a graphics processing unit, and any other electronic components capable of processing data, to execute computer program instructions. The memory may be used to store computer program instructions. In some examples, the measurement method may be implemented by executing computer program instructions in the memory. In some examples, the server 150 may also be a cloud server.

Figure 2:
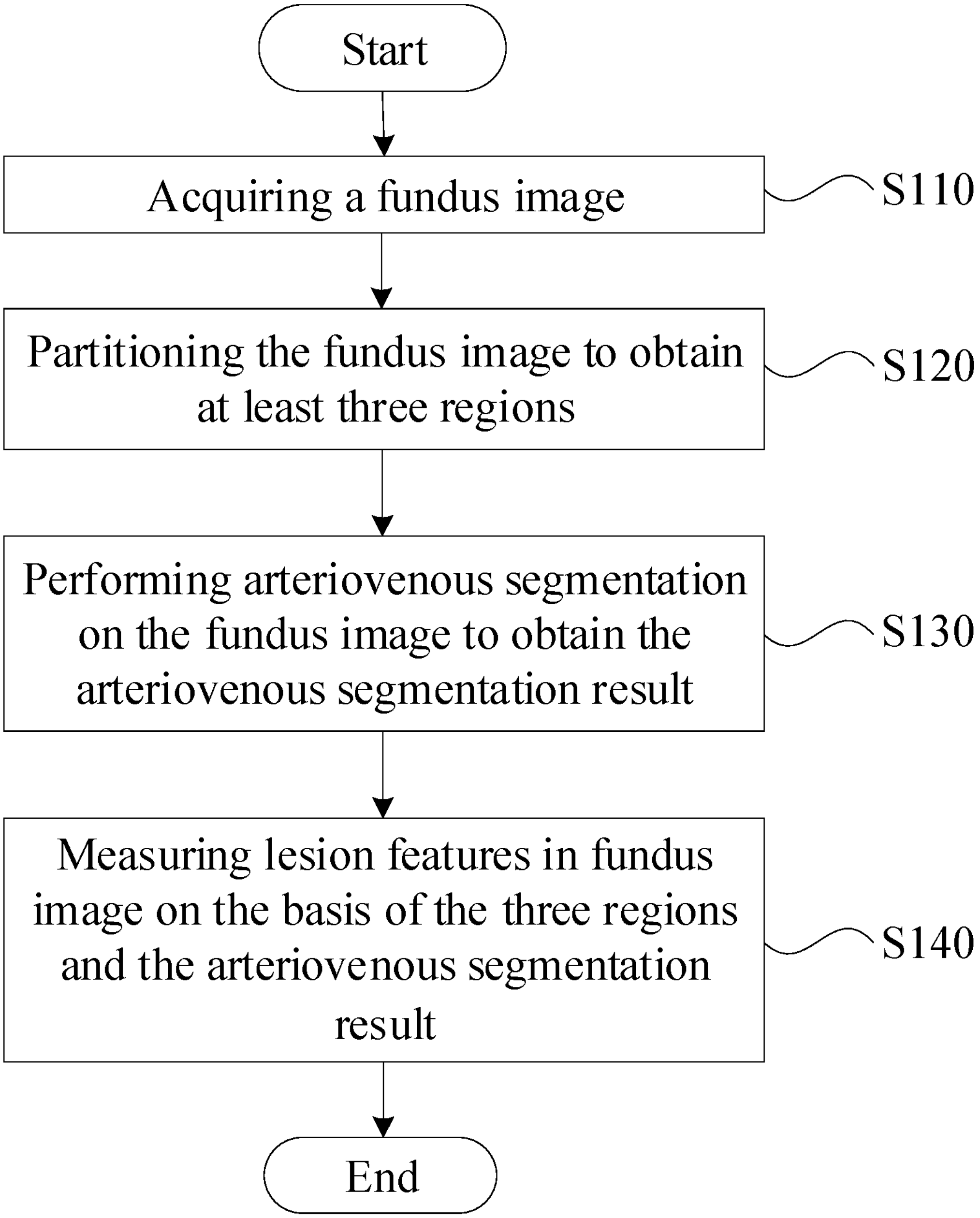
FIG. 2 is a flow chart showing a method for measuring lesion features of hypertensive retinopathy according to an embodiment of the disclosure.
Figure 3:
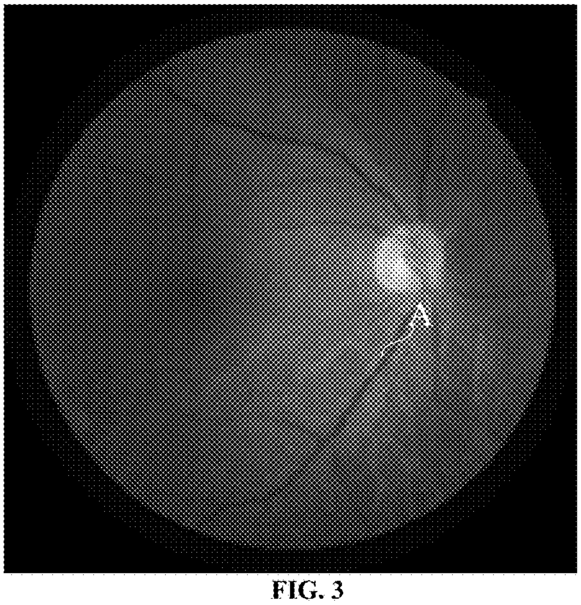
FIG. 3 is a schematic view showing a fundus image according to an embodiment of the disclosure.

FIG. 2 is a flow chart showing a method for measuring lesion features of hypertensive retinopathy according to an embodiment of the disclosure. FIG. 3 is a schematic view showing a fundus image according to an embodiment of the disclosure. In some examples, as shown in FIG. 2, the measuring method may include acquiring a fundus image (step S110), partitioning the fundus image to acquire at least three regions (step S120), performing arteriovenous segmentation on the fundus image to acquire an arteriovenous segmentation result (step S130), and measuring the lesion feature in the fundus image based on the three regions and the arteriovenous segmentation result (step S140). In this case, the lesion features of hypertensive retinopathy in the fundus image may be automatically measured. Thus, the lesion features of hypertensive retinopathy may be measured efficiently and objectively.

In some examples, in step S110, the fundus image may be acquired. In some examples, the fundus image may be a color fundus image. Color fundus images may clearly show fundus information like the inner membrane, retina, macula and vessels (retinal artery and vein) of the eyeball, etc. In other examples, the fundus image may be a grayscale image. In some examples, the fundus image may be a fundus image acquired by the collecting device 130. As an example of a fundus image, FIG. 3 shows a fundus image taken by a fundus camera. The fundus image may include a vessel A. The vessel A may include arteries and veins (not shown).

In some examples, in step S110, the fundus images may be preprocessed. In general, since the fundus images may have possible issues of different image formats and sizes, the fundus images may be preprocessed to convert the fundus images into a fixed standard images. The fixed standard form may mean that the images have the same format and the same size. For example, in some examples, the preprocessed size of the fundus image may have a uniform width of 512 or 1024 pixels.

Figure 4:
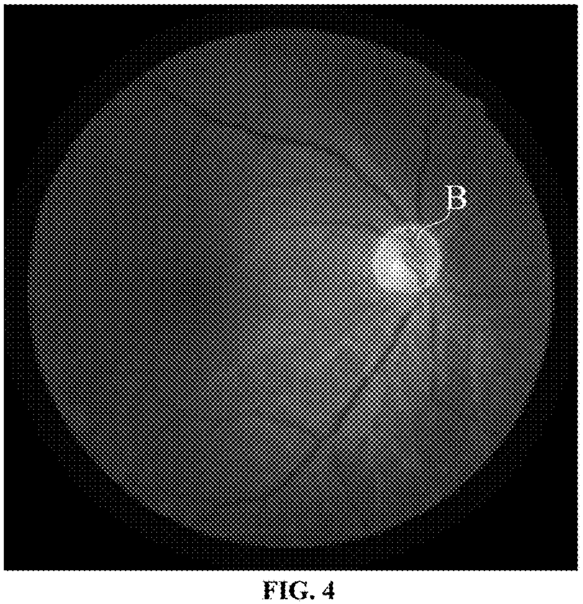
FIG. 4 is a schematic diagram showing an optic disc region according to an embodiment of the disclosure.

FIG. 4 is a schematic diagram showing an optic disc region B according to an embodiment of the disclosure. In some examples, in step S120, the fundus image may be partitioned to obtain at least three regions. In some examples, an optic disc region B (see FIG. 4) of the fundus image may be identified. In some examples, the optic disc region B of the fundus image may be segmented by an image segmentation algorithm to locate the optic disc region B. In some examples, the fundus image may be segmented by a depth learning image segmentation model (e.g., a U-Net model) to locate the optic disc region B. As an example of the optic disc region B, for example, FIG. 4 shows a schematic view of the optic disc region B located by the U-Net model. However, the examples of the present disclosure are not limited thereto. In other examples, the image segmentation algorithm may also be an active contouring, a Grab cut or a threshold value segmentation method, etc.

Figure 5:
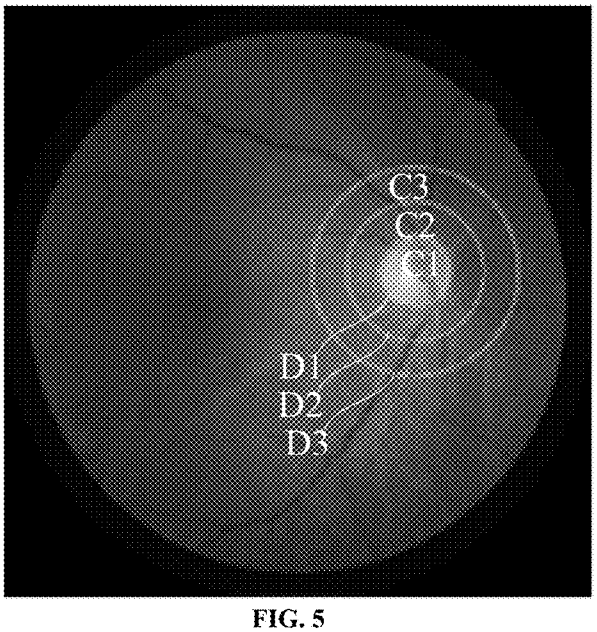
FIG. 5 is a schematic diagram showing three regions of a fundus image according to an embodiment of the disclosure.

FIG. 5 is a schematic diagram showing three regions of a fundus image according to an embodiment of the disclosure.

In some examples, the fundus image may be divided into at least three regions based on the optic disc region B. As shown in FIG. 5, in some examples, the three regions may include a first region C1, a second region C2, and a third region C3. Thus, three regions may be acquired based on the optic disc region B.

In some examples, the first region C1 may be a region of a first circle D1 formed by taking a center of a circumscribed circle of the optic disc region B as the center and a first pre-set multiple of a diameter of the circumscribed circle as the diameter. In some examples, the first pre-set multiple may be represented by v1. In some examples, v1 may be 1. In some examples, the second region C2 may be a region from the edge of the first region C1 to a second circle D2 formed by taking a center of the circumscribed circle as the center and a second pre-set multiple of the diameter of the circumscribed circle as the diameter. In some examples, the second pre-set multiple may be represented by v2. In some examples, v2 may be 2. In some examples, the third region C3 may be a region from the edge of the second region C2 to a third circle D3 formed by taking a center of the circumscribed circle as the center and a third pre-set multiple of a diameter of the circumscribed circle as the diameter. In some examples, the third pre-set multiple may be represented by v3. In some examples, v3 may be 3. In some examples, let $v1<v2<v3$. In other examples, the fundus image may be partitioned in other ways according to actual needs. For example, the first region C1 and the second region C2 may be merged into one region and the third region C3 is taken as another region.

In some examples, in step S130, the arteriovenous segmentation may be performed on the fundus image to obtain an arteriovenous segmentation result. Thus, the arterial and venous regions may be identified, thereby removing the effects of structures other than arteries and veins.

Figure 6:
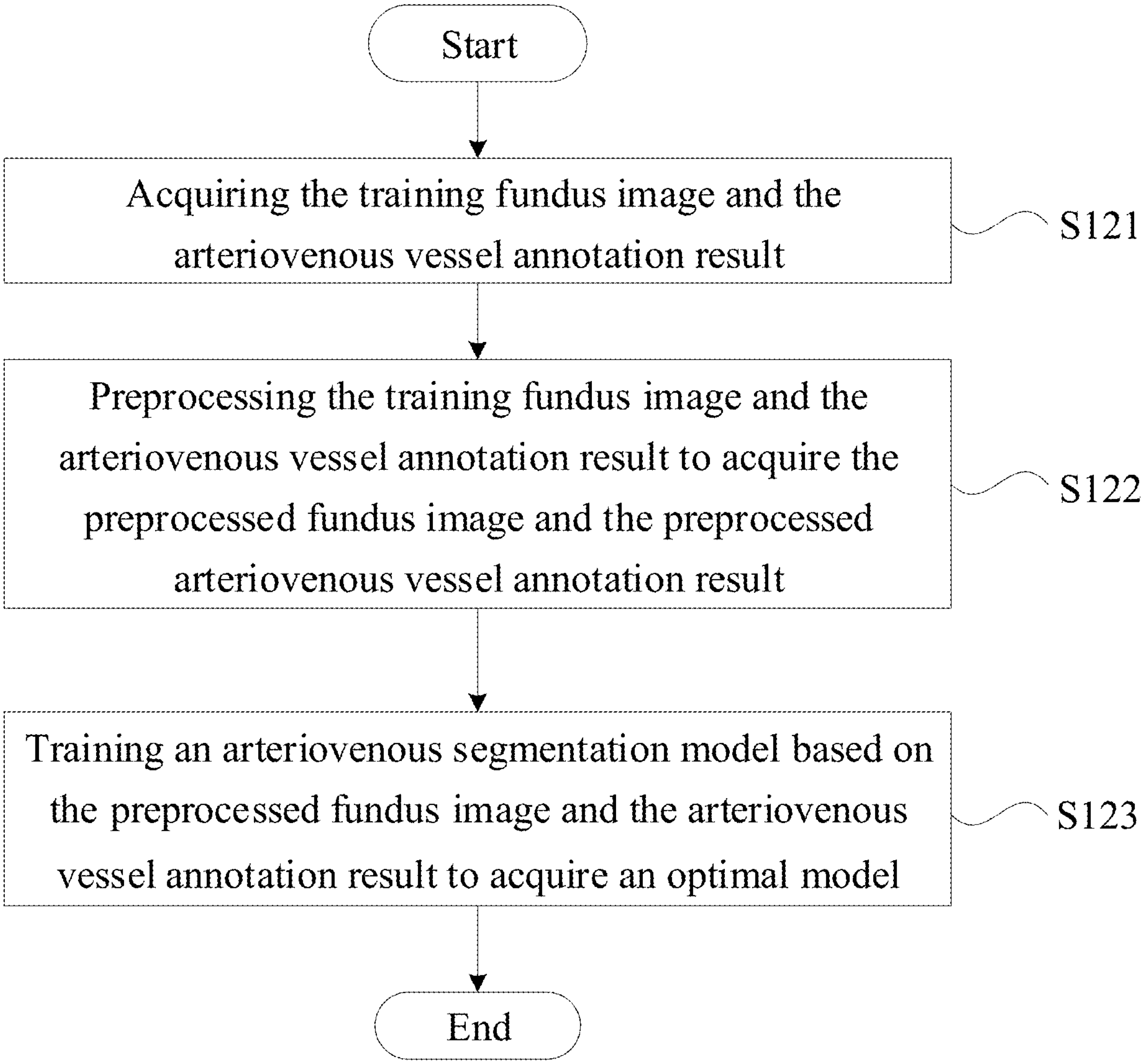
FIG. 6 is a flowchart showing a method of training an arteriovenous segmentation model based on deep learning according to an embodiment of the disclosure.

In some examples, the artery and vein in the fundus image may be segmented to directly obtain an artery segmentation result and a vein segmentation result (i.e., an arteriovenous segmentation result). In some examples, the deep learning-based arteriovenous segmentation model may be trained to perform the arteriovenous segmentation on the fundus image in step S110 by taking the training fundus image and its arteriovenous vessel annotation results as a training set. Hereinafter, a training method of an arteriovenous segmentation model based on deep learning will be described in detail with reference to the accompanying drawings. FIG. 6 is a flowchart showing a method of training an arteriovenous segmentation model based on deep learning according to an embodiment of the disclosure.

As shown in FIG. 6, in some examples, the training method of the arteriovenous segmentation model may include acquiring a training fundus image and an arteriovenous vessel annotation result (step S121), preprocessing the training fundus image and the arteriovenous vessel annotation result to acquire a preprocessed fundus image and a preprocessed arteriovenous vessel annotation result (step S122), and training the arteriovenous segmentation model based on the preprocessed fundus image and the preprocessed arteriovenous vessel annotation result to acquire an optimal model (step S123). In this case, the deep learning-based arteriovenous segmentation model may automatically learn arterial and venous features and output the arteriovenous segmentation results.

Figure 7A:
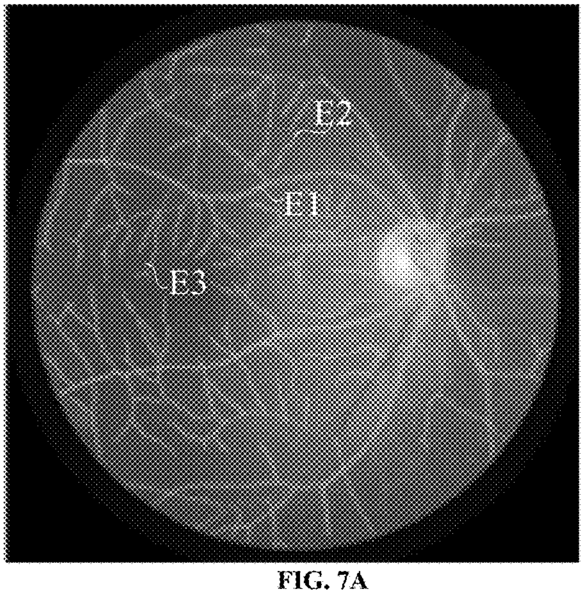
FIG. 7A is a schematic diagram showing arteriovenous vessel annotation results according to an embodiment of the disclosure.
Figure 7B:
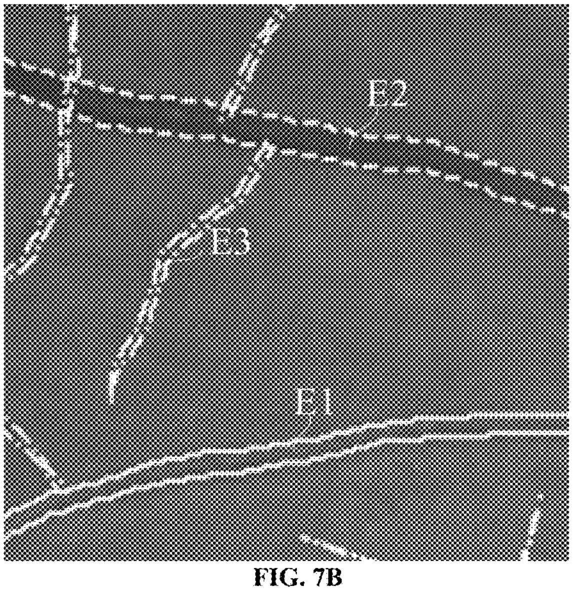
FIG. 7B is a schematic diagram showing a part of the arteriovenous vessel annotation results according to an embodiment of the disclosure.

FIG. 7A is a schematic diagram showing arteriovenous vessel annotation results according to an embodiment of the disclosure. FIG. 7B is a schematic diagram showing a part of the arteriovenous vessel annotation results according to an embodiment of the disclosure. In some examples, in step S121, the training fundus image may be a fundus image obtained by photographing the fundus. In some examples, the training fundus image may be annotated to acquire arteriovenous vessel annotation results for the training fundus image. In some examples, the arteriovenous vessel annotation results may include artery annotation results and vein annotation results (not shown).

In some examples, the arteriovenous vessel annotation results may be formed by annotating vessels in a training fundus image. The vessels may include arteries and veins. In some examples, the arteriovenous vessel annotation results may be formed by annotating boundaries of vessels in a training fundus image. In some examples, the arteriovenous vessel annotation results may be formed by annotating the boundaries of all vessels in the training fundus image.

In some examples, the arteriovenous vessel annotation result may be formed by annotating a boundary of a vessel of a portion in the training fundus image. In general, due to the similarity of vessel features, annotating only the boundaries of vessels with the diameter larger than the pre-set vessel diameter may cause confusion between non-arteriovenous regions (i.e., background) and vessels with the diameter smaller than the pre-set vessel diameter (small vessels for short). Due to the high similarity of vessels with the diameter smaller than the pre-set vessel diameter and vessels with the diameter larger than the pre-set vessel diameter, the annotating only vessels with the diameter larger than the pre-set vessel diameter may seriously affect the accuracy of the arteriovenous segmentation. Therefore, it is necessary to annotate the small vessels, and then the contribution of this region to the loss function may be controlled by adjusting the weight to improve the accuracy of arteriovenous segmentation. In some examples, the pre-set vessel diameter may be 50 μm.

Specifically, the boundary of a vessel with a vessel diameter greater than the pre-set vessel diameter in the training fundus image may be annotated to form an artery annotation result and a vein annotation result, and the direction of a small vessel may be annotated to form a small vessel annotation result, that is, the arteriovenous vessel annotation results may include an artery annotation result E1 greater than the pre-set vessel diameter, a vein annotation result E2 greater than the pre-set vessel diameter, and a small vessel annotation result E3 (see FIG. 7). In calculating the loss function, the weight of the region corresponding to the small vessel annotation result may be adjusted based on the small vessel annotation result. In this case, only annotation of the direction of the small vessel may reduce the annotation difficulty and workload in comparison with accurate annotation of the boundary of the small vessel, thereby reducing annotation cost. By adjusting the weights of the regions corresponding to the small vessel annotation results, the contribution of the small vessel annotation results with only the direction annotated to the loss function may be controlled, and the accuracy of arteriovenous segmentation may be improved.

In some examples, the direction of the small vessel may be a less accurate vessel boundary that may be used to estimate the region corresponding to the small vessel. In some examples, the direction of the small vessel may be any curve that follows the direction of the small vessel. In some examples, in calculation of the loss function, the weight of the region corresponding to the small vessel annotation result may be adjusted to zero. In this case, it is able to exclude the contribution of the small vessel annotation results with only the direction annotated to the loss function. Thus, it is able to avoid the influence of the small vessel annotation result having low accuracy in the arteriovenous segmentation on the arteriovenous segmentation model. It should be noted that while vessels with the diameter larger than the pre-set vessel diameter are trained, some small vessels may still be accurately segmented therefrom due to the similarity of vessel features. In some examples, the region corresponding to the small vessel annotation result may be the fundus region and its distended region corresponding to the small vessel annotation result.

In some examples, the training fundus image may be annotated by an experienced physician using annotation tool to generate arteriovenous vessel annotation results. As an example of an arteriovenous vessel annotation result. For example, FIG. 7A shows an arteriovenous vessel annotation result generated after annotating the training fundus image. The arteriovenous vessel annotation results may include an artery annotation result E1, a vein annotation result E2 and a small vessel annotation result E3. In order to more clearly show the arteriovenous vessel annotation results, FIG. 7B shows the local arteriovenous vessel annotation results. In some examples, the arteriovenous vessel annotation results may also include a background region (not shown).

In some examples, in step S122, the training fundus image may be preprocessed to generate a preprocessed fundus image. In some examples, the preprocessing of the training fundus image may include cropping, denoising, graying, etc. the training fundus image. Thus, vessels in the training fundus image may be highlighted. In some examples, the arteriovenous vessel annotation results may be preprocessed to generate preprocessed arteriovenous vessel annotation results. In some examples, the arteriovenous vessel annotation results may be preprocessed in the same manner as the training fundus image is preprocessed.

In some examples, in step S123, the preprocessed arteriovenous vessel annotation result may be taken as a true value to calculate a loss function, and the arteriovenous segmentation model is continuously optimized by the loss function until the value of the loss function (i.e., loss) converges to an optimum to obtain an optimum model. In some examples, the optimal model may output the probability that each pixel point in the preprocessed fundus image belongs to an artery, a vein or a background, thereby being able to identify a region of an artery and a region of a vein matching the preprocessed arteriovenous vessel annotation result, thereby directly obtaining an artery segmentation result and a vein segmentation result (i.e., an arteriovenous segmentation result). Thus, the arteriovenous segmentation model may directly obtain the arteriovenous division result. In some examples, the arteriovenous segmentation model may be a U-Net model.

Figure 8:
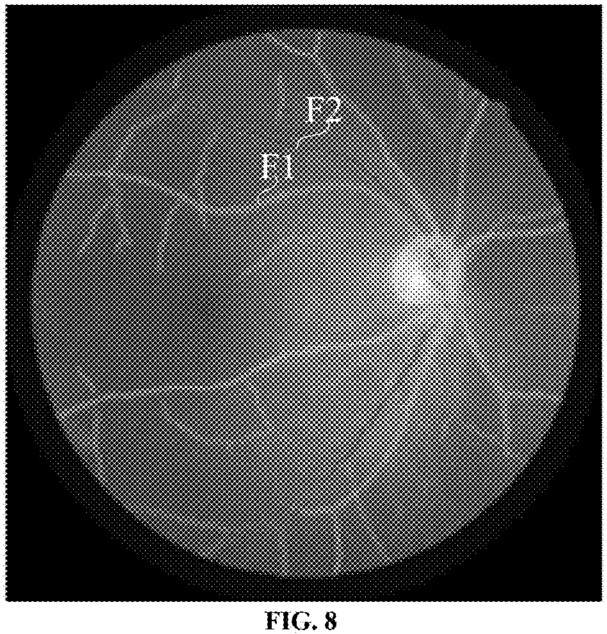
FIG. 8 is a schematic diagram showing an arteriovenous segmentation result according to an embodiment of the disclosure.

FIG. 8 is a schematic diagram showing an arteriovenous segmentation result according to an embodiment of the disclosure. In some examples, the fundus image acquired in step S110 may be input into an optimal model obtained by the above-mentioned training method to perform arteriovenous segmentation on the fundus image, thereby generating an arteriovenous segmentation result. As an example of the arteriovenous segmentation result, FIG. 8 shows an arteriovenous segmentation result generated by performing arteriovenous segmentation on a fundus image. The arteriovenous segmentation results may include an artery segmentation result F1 and a vein segmentation result F2. In some examples, the arteriovenous segmentation result may be a ternary image. In some examples, the ternary image may include three grayscale values representing an artery, a vein, and a background, respectively.

However, the disclosed examples are not limited thereto. In other examples, the vessel segmentation may be first performed on the fundus image to obtain a vessel segmentation result (i.e., the artery and vein are not distinguished first), and then the artery and vein may be classified based on the vessel segmentation result to obtain an artery segmentation result F1 and a vein segmentation result F2.

In some examples, in step S140 of the measurement method, the lesion features of hypertensive retinopathy in the fundus image may be measured based on the three regions and the arteriovenous segmentation result. In some examples, the lesion features may include at least one of arteriovenous cross-indentation features, arteriolar local stenosis features, and arteriolar general stenosis features. For example, the lesion feathers may be one of arteriovenous cross-indentation features, arteriolar local stenosis features, and arteriolar general stenosis features. For example, the lesion features may be arteriovenous cross-indentation features and arteriolar local stenosis features, arteriovenous cross-indentation features and arteriolar general stenosis features, arteriolar local stenosis features and arteriolar general stenosis features, etc. In some examples, the lesion features may be arteriovenous cross-indentation features, arteriolar local stenosis features, and arteriolar general stenosis features.

As described above, although it is trained for vessels with the diameter larger than the pre-set vessel diameter, small vessels may still be segmented therefrom due to the similarity of vessel features. In some examples, vessels with the diameter larger than the pre-set vessel diameter in the arteriovenous segmentation result may be filtered for measurement of lesion features. The examples of the present disclosure are not so limited and. In other examples, the vessels may be used directly for the measurement of lesion features without being filtered. Thus, the accuracy of lesion feature measurement may be further improved.

Figure 9:
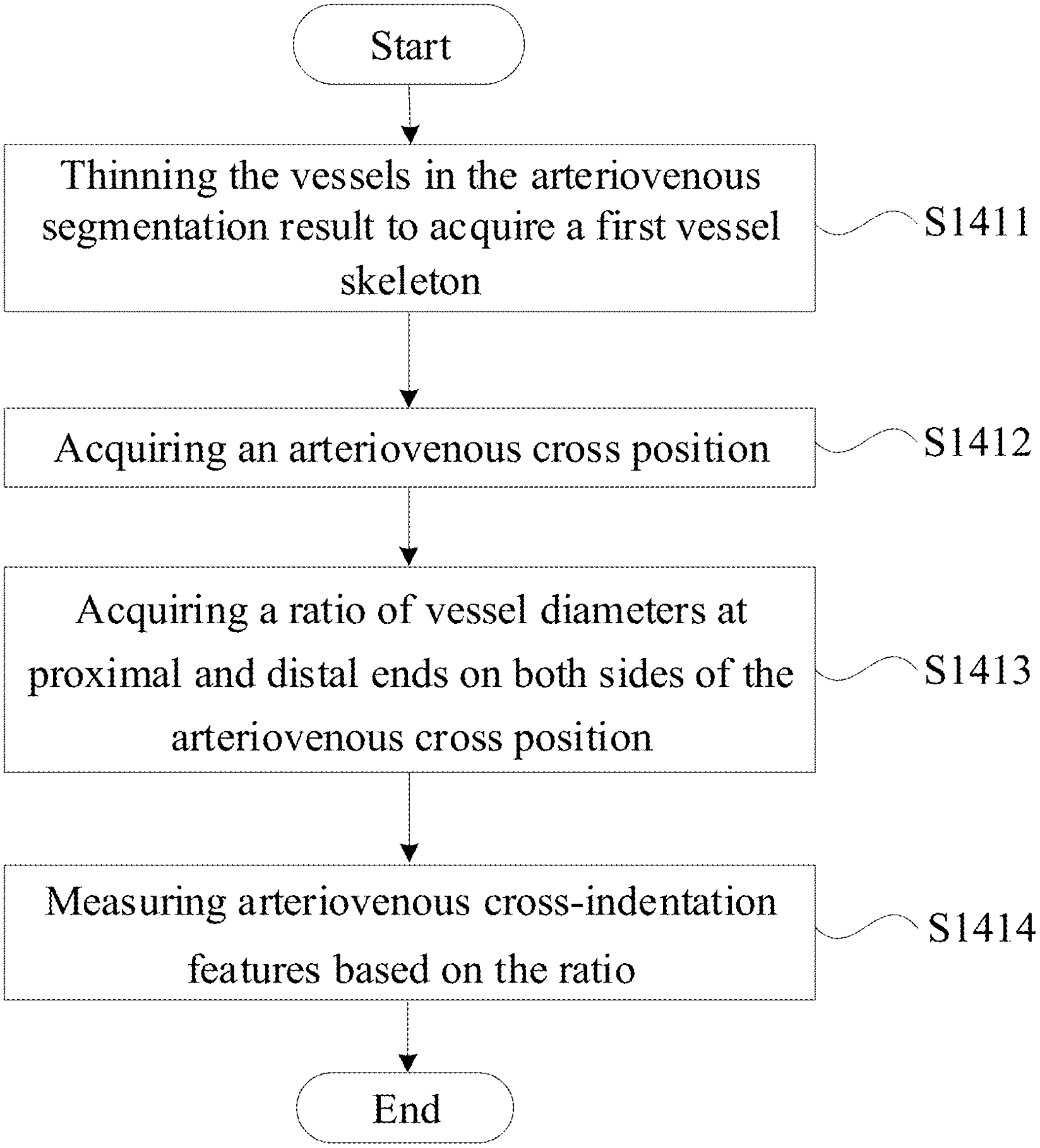
FIG. 9 is a flow chart showing the measurement of arteriovenous cross-indentation features according to an embodiment of the disclosure.

FIG. 9 is a flow chart showing the measurement of arteriovenous cross-indentation features according to an embodiment of the disclosure. As shown in FIG. 9, in some examples, the measurement of the arteriovenous cross-indentation features may include specifying the vessels in the arteriovenous segmentation result to acquire a first vessel skeleton (step S1411), acquiring an arteriovenous cross position (step S1412), acquiring a ratio of proximal and distal vessel diameters on both sides of the arteriovenous cross position (step S1413), and measuring the arteriovenous cross-indentation features based on the ratio (step S1414).

In some examples, in step S1411, the vessels in the arteriovenous segmentation result may be thinned to obtain a first vessel skeleton. In general, the nerve fibers in the first region C1 and the second region C2 are dense so that it seems to show vascular stenosis at the arteriovenous cross position, which does not fall into the category of measuring the arteriovenous cross-indentation features. In this case, the results of the arteriovenous segmentation of the fundus region except for both the first region C1 and the second region C2 may be thinned to obtain the first vessel skeleton. In some examples, the first vessel skeleton may include a plurality of skeleton pixel points as first measurement pixel points. The fundus region may be a region within the contour of the eyeball. In some examples, the arteriovenous segmentation results may be thinned by a morphological thinning algorithm. In some examples, the morphological thinning algorithm may include, but is not limited to, a Hilditch thinning algorithm, a Pavlidis thinning algorithm, or a Rosenfeld thinning algorithm, and so on.

In some examples, in step S1412, an arteriovenous cross position may be obtained. In some examples, the number of skeleton pixel points within a predetermined range of the respective first measurement pixel points of the first vessel skeleton may be acquired as a first adjacent point number. In some examples, the first measured pixel point having a first adjacent point number greater than a first predetermined number may be acquired as a cross point. In some examples, the pixel point corresponding to the cross point in the arteriovenous segmentation result may be taken as the arteriovenous cross position. In some examples, the pre-set range may be eight neighborhoods around the first measurement pixel point. In some examples, the first predetermined number may be three.

Since the vein segmentation result F2 may be discontinuous at the arteriovenous cross position, which is generally shown that the artery segmentation result F1 and the vein segmentation result F2 do not intersect at the arteriovenous cross position, resulting in that part of the arteriovenous cross position cannot be directly obtained by step S1411 and step S1412. In some examples, the artery segmentation result F1 may be expanded such that the expanded artery segmentation result F1 intersects the vein segmentation result F2 to determine the arteriovenous cross position. Specifically, the crossed expanded artery segmentation result F1 and vein segmentation result F2 may be thinned to obtain a vessel skeleton, and an arteriovenous cross position may be determined based on the vessel skeleton. Specific contents refer to the relevant description of acquiring the arteriovenous cross position based on the first vessel skeleton in step S1411 and step S1412. Thereby, a more accurate arteriovenous cross position may be acquired.

In some examples, the maximum vessel diameter may be a predicted maximum vessel diameter. In some examples, the predicted maximum vessel diameter may be twice a maximum distance of skeleton pixel points on the first vessel skeleton from their nearest non-vessel pixels. The distance may be a Euclidean distance. Specifically, the Euclidean distance between each skeleton pixel point and its nearest non-vessel pixel is calculated, and 2 times of the maximum Euclidean distance is selected as a predicted maximum vessel diameter. However, the examples of the present disclosure are not limited hereto. In other examples, the maximum vessel diameter may be predicted using other means.

In some examples, in step S1413, the ratio of the vessel diameters at the proximal and distal ends of the vein segmentation result F2 on both sides of the arteriovenous cross position in the arteriovenous segmentation result may be calculated. In some examples, the proximal and distal ends on both sides of the arteriovenous cross position may be proximal and distal ends of the arteriovenous segmentation results along the direction of extension of the vein division result F2 and on each of both sides of the arteriovenous cross position.

In some examples, if the vein segmentation result F2 is discontinuous at the arteriovenous cross position in the arteriovenous segmentation result, the proximal end of each side may be the skeleton pixel point on the first vessel skeleton of the vein segmentation result F2 which is closest to the arteriovenous cross position. In some examples, if the vein segmentation result F2 in the arteriovenous segmentation results is continuous at the arteriovenous cross position, the proximal end of each side may be the arteriovenous cross position. In some examples, the distal end of each side may be a skeleton pixel point on the first vessel skeleton of the vein segmentation result F2 to which a distance from the arteriovenous cross position is a first pre-set distance. Thus, the proximal and distal ends of both sides of the vein segmentation result may be determined based on the arteriovenous cross position. In some examples, the first pre-set distance may be 2 to 4 times of the maximum vessel diameter. In some examples, the first pre-set distance may be three times of the maximum vessel diameter.

In some examples, in step S1413, the arteriovenous segmentation result may be intercepted with the arteriovenous cross position as the center of circle and with 4 to 6 times of the maximum vessel diameter as the radius. Thus, the artery segmentation result F1 and the vein segmentation result F2 in the vicinity of each arteriovenous cross position may be conveniently displayed.

In some examples, in step S1414, the arteriovenous cross-indentation features may be measured based on the ratio. In some examples, the presence of arteriovenous cross-indentation features are present if the ratio of both sides is not greater than 1/2. In some examples, if a ratio of not greater than 1/2 is present on only one side, the presence of suspected arteriovenous cross-indentation features is indicated. In some examples, if the ratios are greater than 1/2 on both sides, the absence of arteriovenous cross-indentation features is indicated.

Figure 10:
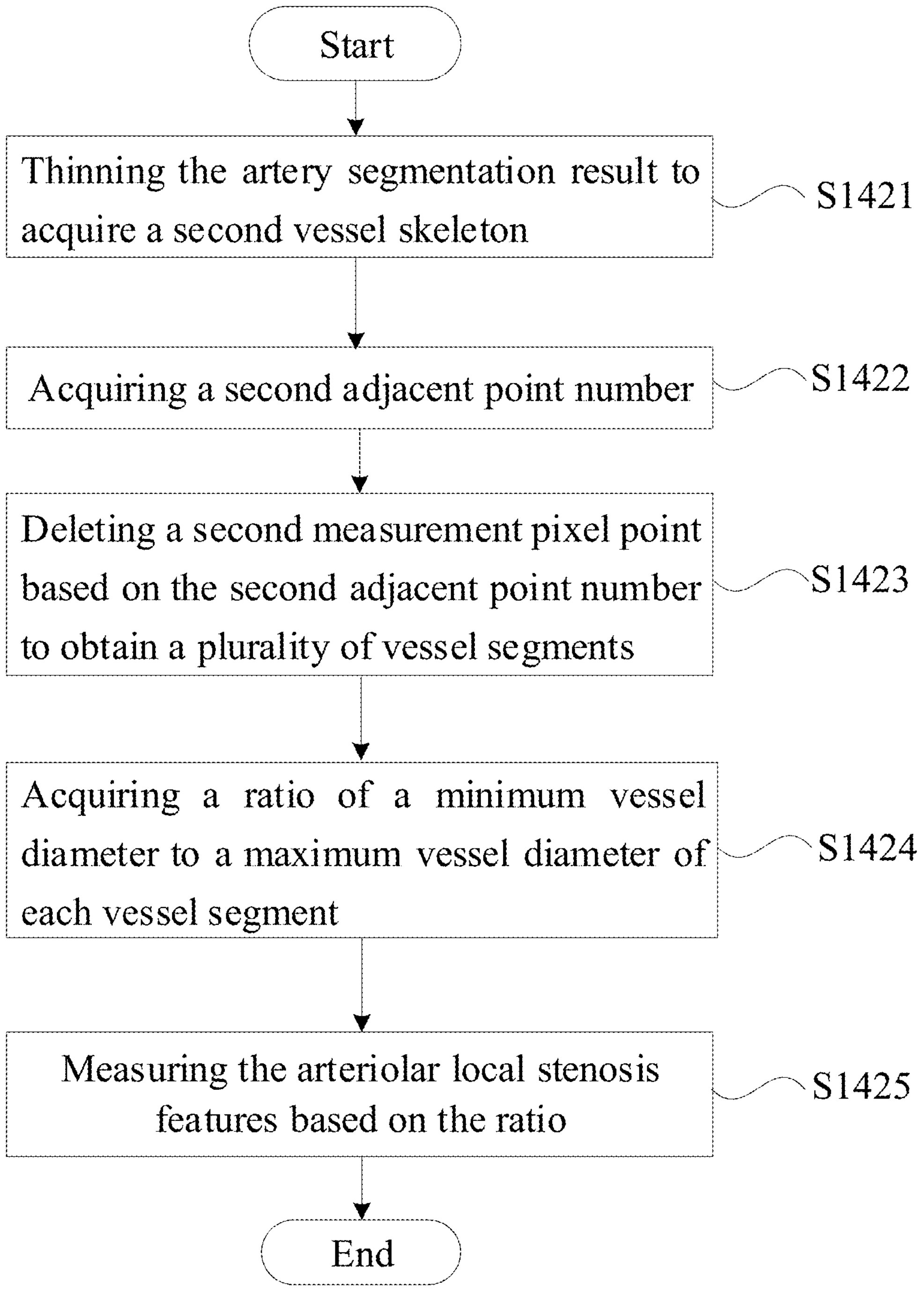
FIG. 10 is a flow chart showing the measurement of arteriolar local stenosis features according to an embodiment of the disclosure.

FIG. 10 is a flow chart showing the measurement of arteriolar local stenosis features according to an embodiment of the disclosure. As described above, the lesion features may include arteriolar local stenosis features. As shown in FIG. 10, in some examples, the measurement of the arteriolar local stenosis feature may include thinning the artery segmentation result to obtain a second vessel skeleton (step S1421), acquiring a second adjacent point number (step S1422), deleting the second measurement pixel points based on the second adjacent point number to obtain a plurality of vessel segments (step S1423), acquiring a ratio of a minimum vessel diameter to a maximum vessel diameter for each vessel segment (step S1424), and measuring the arteriolar local stenosis features based on the ratio (step S1425).

In some examples, in step S1421, the artery segmentation result F1 having the vessel diameter larger than the pre-set vessel diameter may be thinned to obtain a second vessel skeleton. See the relevant description in step S1411 for the relevant description of the thinning process. In some examples, the second vessel skeleton may include a plurality of skeleton pixel points taken as second measurement pixel points. In some examples, the pre-set vessel diameter may be 50 μm.

In some examples, in step S1422, the number of skeleton pixel points within the pre-set range of the respective second measurement pixel points may be taken as the second adjacent point number. In some examples, the pre-set range may be eight neighborhoods around the second measurement pixel point.

In some examples, in step S1423, a second measurement pixel point having a second adjacent point number greater than a second pre-set number may be deleted to obtain a plurality of vessel segments. In some examples, the second predetermined number may be 2.

In some examples, in step S1424, the vessel diameter of each vessel segment at each skeleton pixel point may be calculated, and the ratio of the minimum vessel diameter $w_{min}$ to the maximum vessel diameter $w_{max}$ of each vessel segment is obtained. In some examples, in step S1425, the arteriolar local stenosis features may be measured based on the ratio. In some examples, if $w_{min}/w_{max} \geq 2/3$, there is no presence of arterial local stenosis feature, otherwise there is presence of an arterial local stenosis feature.

As noted above, the lesion features may include arteriolar general stenosis features. In some examples, an artery vessel segment and a vein vessel segment within the third region C3 of the arteriovenous segmentation results may be acquired when measurements are performed for the arteriolar general stenosis features. In some examples, an arteriole-to-venule ratio (AVR) may be obtained based on an arterial vessel segment, a vein vessel segment, and a pre-set formula. In some examples, the arteriolar general stenosis features may be measured based on the arteriole-to-venule ratio. Thus, the arteriolar general stenosis features may be measured based on the artery vessel segment and the vein vessel segment in the third region C3. In some examples, the arteriole-to-venule ratio may be a ratio of a central retinal artery equivalent diameter (CRAE) to a central retinal vein equivalent diameter (CRVE).

In some examples, the pre-set formula may be a modified formula of Knudtson. Thus, the arteriolar general stenosis features may be measured based on the modified formula of Knudtson. Specifically, taking the modified formula of Knudtson as an example, the process of measuring the arteriolar general stenosis features is introduced. In general, the artery vessel segment and the vein vessel segment in the third region C3 are independent vessel segments. In some examples, if bifurcated vessel segments are present, the above description of obtaining vessel segments in measuring the arteriolar local stenosis features may be for reference.

In some examples, the central retinal artery equivalent diameter CRAE may be iteratively obtained from the vessel diameter of the arterial vessel segment within the third region C3. In the calculation, an arterial vessel segment with a largest vessel diameter may be paired with an arterial vessel segment with a smallest vessel diameter, an arterial vessel segment with a second largest vessel diameter may be paired with an arterial vessel segment with a second smallest vessel diameter, and so on, and it may be iterated according to Formula (1) to calculate the central retinal artery equivalent diameter CRAE:

$$w = 0.88 \times (w_1^2 + w_2^2)^{\frac{1}{2}}. \quad (1)$$

Here, $w_1$ is a smaller diameter, and $w_2$ is a larger diameter. The resulting intermediate values $w$ continue to serve as vessel diameters and iterate as described above until only one intermediate value $w$ remains and the intermediate value $w$ is taken as the central retinal artery equivalent diameter CRAE. In some examples, if the number of arterial vessel segments is odd, the vessel diameter of a single arterial vessel segment may be left for the next iteration.

In some examples, it may be iterated according to Formula (2) based on the vein vessel segment to calculate the central retinal vein equivalent diameter CRVE:

$$x = 0.95 \times (x_1^2 + x_2^2)^{\frac{1}{2}}. \quad (2)$$

Here, $x_1$ is a smaller vessel diameter, $x_2$ is a larger vessel diameter, and $x$ is a resulting intermediate value. See the relevant description of calculating the central retinal artery equivalent diameter CRAE for specific contents.

Through the above steps, the central retinal artery equivalent diameter CRAE and the central retinal vein equivalent diameter CRVE may be obtained, and then the formula for the arteriole-to-venule ratio AVR may be as shown in Formula (3): AVR=CRAE/CRVE (3). In some examples, if AVR is less than 2/3, then an arteriolar general stenosis feature is present, otherwise there is no presence of arteriolar general stenosis features.

Figure 11:
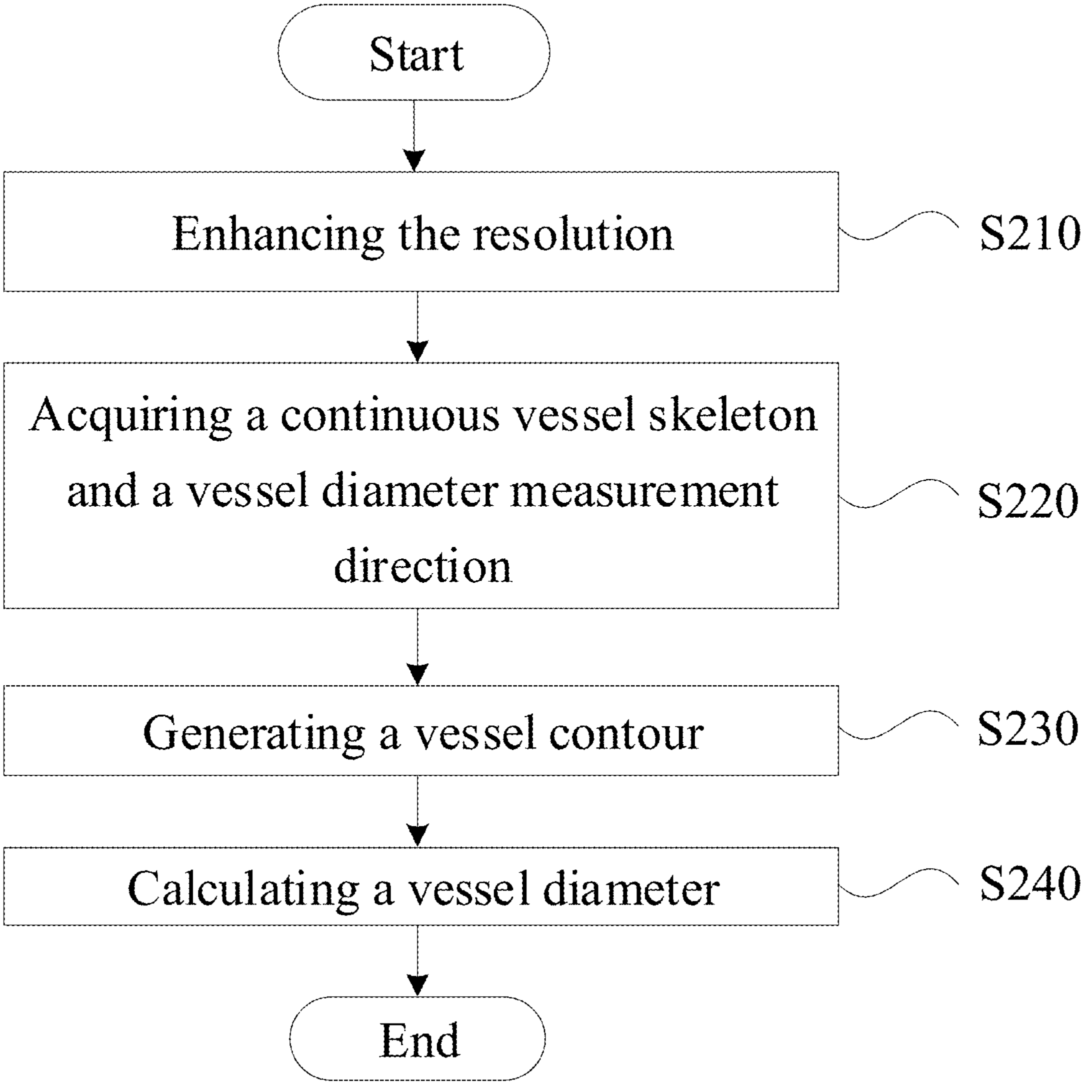
FIG. 11 is a flow chart showing the measurement of vessel diameter according to an embodiment of the disclosure.

FIG. 11 is a flow chart showing the measurement of vessel diameter according to an embodiment of the disclosure. In some examples, as shown in FIG. 11, the measurement of the aforementioned vessel diameters may include enhancing the resolution (step S210), acquiring a continuous vessel skeleton and a vessel diameter measurement direction (step S220), generating a vessel contour (step S230), and calculating vessel diameters (step S240). In this case, the resolution of the vessel in the fundus image may be increased and the vessel diameter may be measured with more pixels. Thus, it is able to perform automatic super-resolution measurement of the vessel diameter and improve the measurement accuracy of the vessel diameter.

In general, the width (i.e., the number of pixels) measured for the vessel diameter in the fundus image is a positive integer. For example, the measured width may be 1, 3, 6, or 8, etc. However, a super-resolution technique based on resolution enhancement and pre-set accuracy may perform sub-pixel-level measurement on the vessel diameter, so that the measurement width may be decimal. For example, the measurement width may be 1.23, 3.12, 5.63 or 7.56, etc. Thereby, the vessel diameter may be measured more accurately.

In some examples, in step S210, the arteriovenous segmentation result may be a binary image, and as described above, the arteriovenous segmentation result may be a ternary image. In some examples, the arteriovenous segmentation results may be converted to a binary image for vessel diameter measurement by whether they belong to vessel pixel points or not. The vessel pixels are white and the non-vessel pixels are black. However, the examples of the present disclosure are not limited hereto. In other examples, the vessel diameter may be directly measured using a ternary image. In some examples, the arteriovenous segmentation results may be resolution enhanced by a pre-set multiple to generate enhanced arteriovenous segmentation results. For example, in some examples, a 10-times resolution enhancement may be performed on an arteriovenous segmentation result having a resolution size of 140×63 to generate an enhanced arteriovenous segmentation result having a resolution size of 1400×630.

Additionally, in some examples, the arteriovenous segmentation results may be resolution enhanced using a linear interpolation method. However, the examples of the present disclosure are not limited hereto. In other examples, the arteriovenous segmentation results may be resolution enhanced using a depth learning based image super-resolution method. Additionally, in some examples, the pre-set multiple may be an integer greater than 1. Thus, the resolution of the vessel in the fundus image may be increased, and the measurement accuracy of the subsequent measurement of the vessel diameter may be improved. In some examples, the pre-set multiple may be 5 to 15. For example, the pre-set multiple may be 5, 10, or 15, etc.

In some examples, in step S220, after the enhanced arteriovenous segmentation results generated in step S210 is acquired, a vessel skeleton (which may also be referred to as a vessel centerline) in the enhanced arteriovenous segmentation results may be extracted. The vessel skeleton may be the midline of the vessel. In some examples, the vessel skeleton is composed of discrete pixel points. In some examples, in step S220, the enhanced arteriovenous segmentation results may be thinned using a morphological thinning algorithm to extract the vessel skeleton. That is, the vessel width in the enhanced arteriovenous segmentation result is thinned to a pixel width in the direction of the vessel center, forming a vessel skeleton, and keeping the basic topology structure of the vessel shape in the enhanced arteriovenous segmentation result unchanged. In some examples, a median filtering operation may be performed on the enhanced arteriovenous segmentation results prior to performing the vessel skeleton extraction on the enhanced arteriovenous segmentation results. Thus, a possible bifurcation at the end of the vessel skeleton may be removed. In some examples, the vessel skeleton may be fitted to acquire a continuous vessel skeleton. In some examples, the vessel skeleton may be fit by a least squares cubic spline interpolation algorithm. Thus, the continuous vessel skeleton and fitting equations may be obtained.

Figure 12:
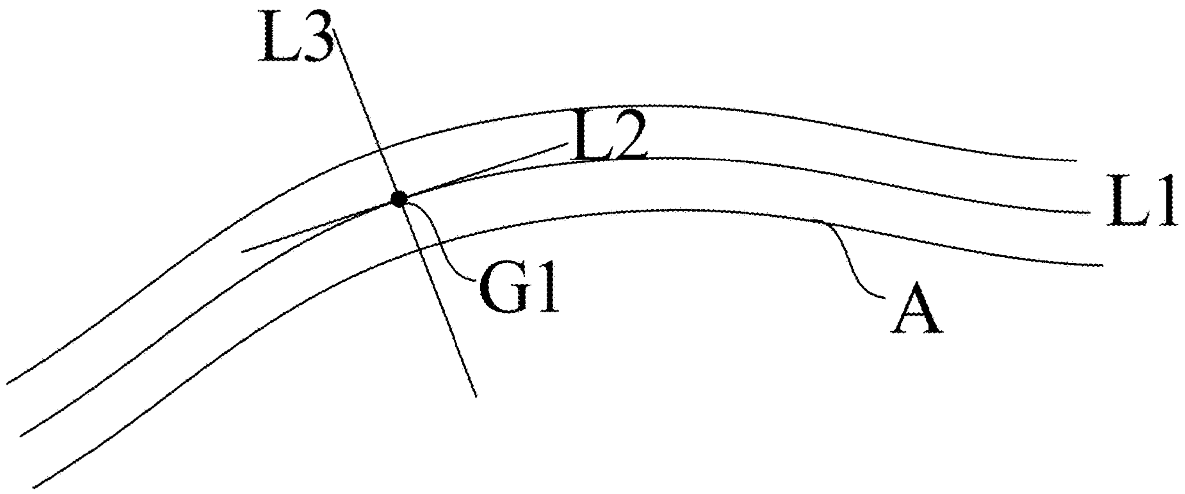
FIG. 12 is a schematic view showing a diameter measurement direction according to an embodiment of the disclosure.

FIG. 12 is a schematic view showing a diameter measurement direction according to an embodiment of the disclosure. Additionally, in some examples, in step S220, the third measurement pixel point may be a plurality of pixel points on the continuous vessel skeleton. In some examples, the vessel diameter measurement direction may be perpendicular to a tangent of the continuous vessel skeleton at a third measurement pixel point. In some examples, the tangent to the third measurement pixel point may be obtained from the first derivative of the fitting equation described above. As shown in FIG. 12, a tangent line of a continuous vessel skeleton L1 of a vessel A at the third measurement pixel G1 may be a tangent line L2. A straight line passing through the third measurement pixel point G1 and perpendicular to the tangent line L2 may be a vessel diameter measurement direction L3.

In some examples, in step S230, a vessel contour corresponding to the third measurement pixel point may be generated based on the enhanced arteriovenous segmentation result obtained in step S210, the third measurement pixel point obtained in step S220, the vessel diameter measurement direction of the third measurement pixel point obtained in step S220, and the pre-set accuracy. In some examples, an interpolation operation may be performed on the enhanced arteriovenous segmentation result by the interpolation algorithm based on the enhanced arteriovenous segmentation result, the third measurement pixel point, the vessel diameter measurement direction of the third measurement pixel point, and the pre-set accuracy, to generate a vessel contour corresponding to the third measurement pixel point. Thereby, the interpolation operation may be performed on the enhanced vessel image based on the pre-set accuracy to obtain a vessel contour. In some examples, the interpolation algorithm may be a cubic spline interpolation algorithm. Thus, the enhanced arteriovenous segmentation results may be interpolated using the cubic spline interpolation algorithm. Additionally, in some examples, the pre-set accuracy may be a decimal greater than zero and less than one. Thus, the resolution of the vessel in the fundus image may be increased, and the measurement accuracy of the subsequent measurement of the vessel diameter may be improved. In some examples, the pre-set accuracy may be 0.01 to 0.10. For example, the pre-set accuracy may be 0.01, 0.05, or 0.10, etc.

Figure 13:
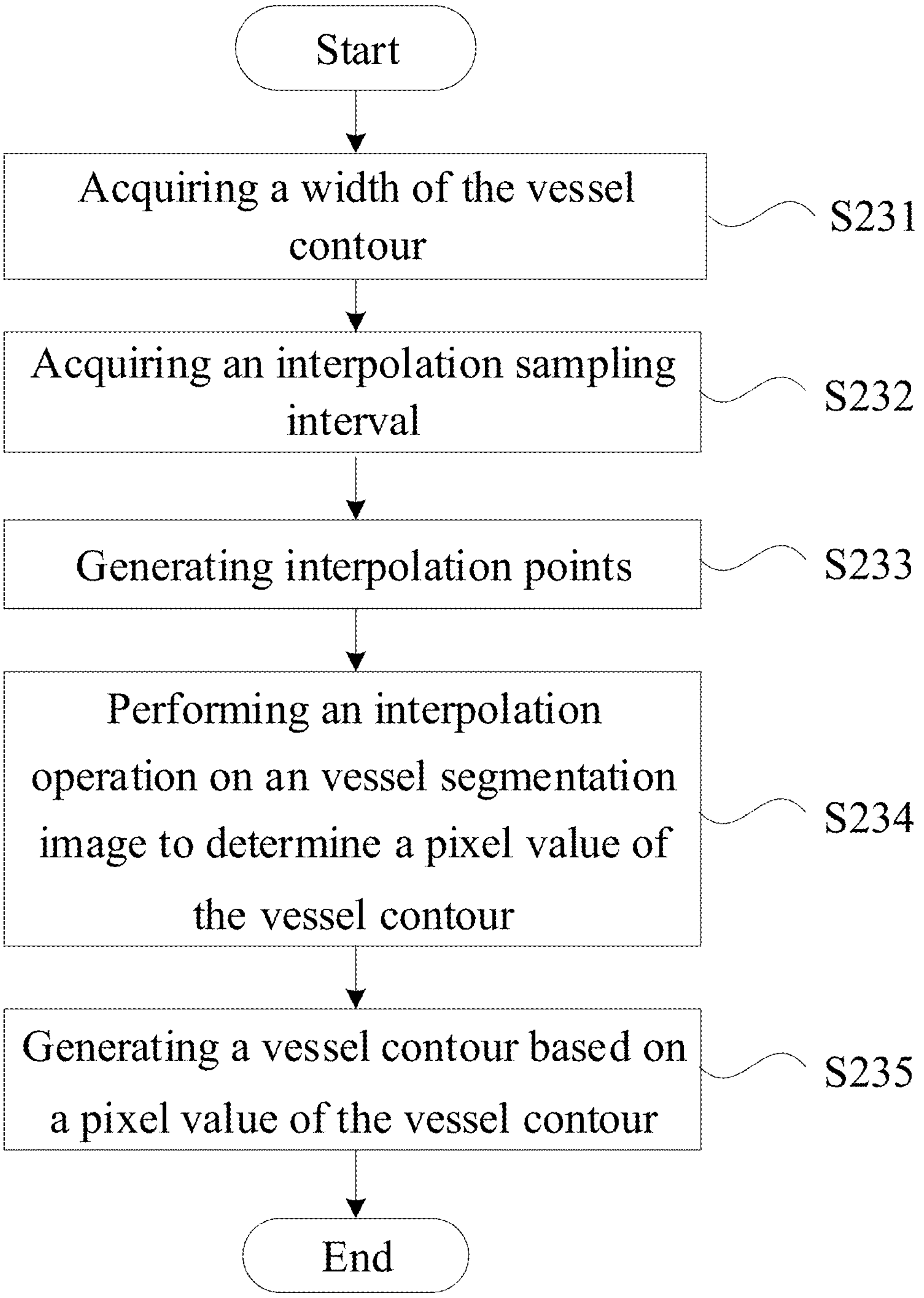
FIG. 13 is a flow chart showing vessel contour generation according to an embodiment of the disclosure.

Hereinafter, the generation process of the vessel contour will be described in detail with reference to the accompanying drawings. FIG. 13 is a flow chart showing vessel contour generation according to an embodiment of the disclosure. As shown in FIG. 13, in some examples, the generation of the vessel contour in step S230 may include acquiring a width of the vessel contour (step S231), acquiring an interpolation sampling interval (step S232), generating an interpolation point (step S233), performing an interpolation operation on the result of the arteriovenous segmentation to determine a pixel value of the vessel contour (step S234), and generating the vessel contour based on the pixel value of the vessel contour (step S235).

In some examples, in step S231, the width of the vessel contour may be N times of the maximum vessel diameter. Here, N may be an integer between 2 and 5. In some examples, the width of the vessel contour may be twice of the maximum vessel diameter. In some examples, the maximum vessel diameter may be a predicted maximum vessel diameter, and reference may be made to the relevant description about the maximum vessel diameter in step S1413. Thereby, the widest vessel in the enhanced arteriovenous segmentation result may be presented intactly in the vessel contour.

In some examples, an interpolation sampling interval may be acquired based on the pre-set accuracy and the width of the vessel contour in step S232. Specifically, it is assumed that the width of the vessel contour may be represented by wi and the pre-set accuracy may be represented by s. The value of the interpolation sampling interval may then be a value between −(wi−1)/2 and (wi−1)/2, incremented by the pre-set accuracy s. For example, the value of the interpolation sampling interval may be −(wi−1)/2, (wi−1)/2+s, (wi−1)/2+2×s, or (wi−1)/2, etc.

In some examples, in step S233, interpolation points may be generated based on the interpolation sampling interval, the diameter measurement direction, and the continuous vessel skeleton obtained in step S232. Specifically, assuming that the interpolation sampling interval is represented by inc, the vessel diameter measurement direction may be represented by (dx, dy), and the continuous vessel skeleton may be represented by (x, y). The interpolation points may then be expressed as (x+dx×inc, y+dy×inc). In this case, the generated interpolation points are distributed along the vessel diameter measurement direction. Thus, the number of pixel points in the vicinity of the vessel diameter measurement direction may be increased, and the measurement accuracy of the vessel diameter may be improved.

In some examples, in step S234, in some examples, an interpolation operation may be used for the results of the arteriovenous segmentation result based on the interpolation points obtained in step S233 to determine a pixel value of the vessel contour. In some examples, the interpolation algorithm may be a cubic spline interpolation algorithm. Thus, the enhanced arteriovenous segmentation results may be interpolated using the cubic spline interpolation algorithm.

Figure 14:
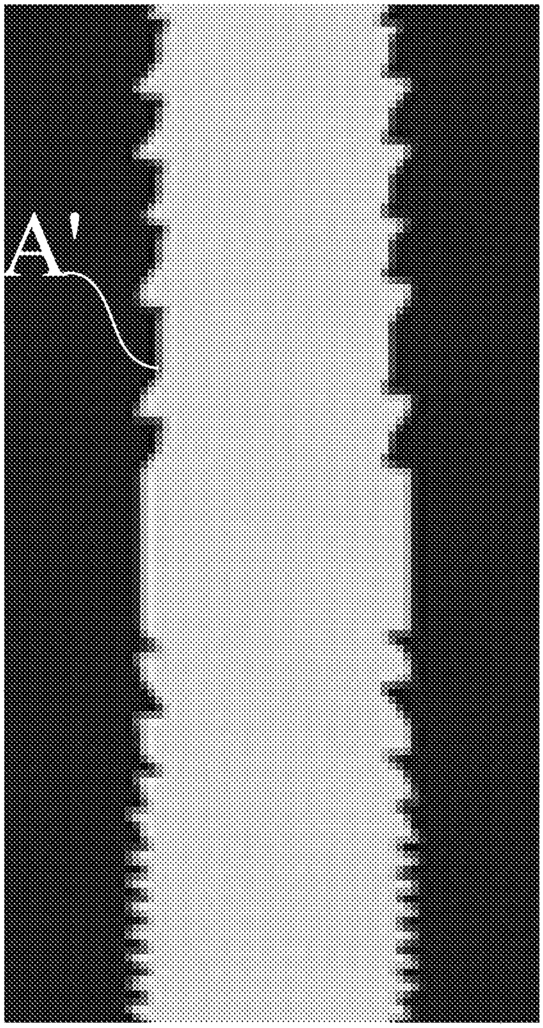
FIG. 14 is a schematic diagram showing an image of a straightened vessel according to an embodiment of the disclosure.

FIG. 14 is a schematic diagram showing an image of a straightened vessel according to an embodiment of the disclosure. In some examples, in step S235, the vessel contour corresponding to each third measurement pixel point may be output based on the pixel value of the vessel contour. In some examples, the vessel contours corresponding to the respective third measurement pixel points may be arranged side by side in a central collinear manner in the order of arrangement of the third measurement pixel points on the continuous vessel skeleton to form a straightened vessel image. As an example of straightening the vessel image, FIG. 14 shows a straightened vessel image. The straightened vessel A' is a vessel after being straightened. Thereby, a vessel contour corresponding to each third measurement pixel point may be conveniently acquired.

In some examples, in step S240 of measuring the vessel diameter, the vessel diameter corresponding to the third measurement pixel point may be calculated based on the number of vessel pixel points in the vessel contour corresponding to the third measurement pixel point, the pre-set multiple and the pre-set accuracy. The vessel contour corresponding to the third measurement pixel point may be obtained by step S230. In some examples, the number n of vessel pixel points in the vessel contour corresponding to the third measurement pixel point may be calculated by the following formula: $n=\text{card}(\{p: P\in P, f(p)>T\})$. Here, p is a third measurement pixel point, f(p) is a pixel value corresponding to the third measurement pixel point p, T is a pre-set threshold parameter, P is a pixel point set in a vessel contour corresponding to the third measurement pixel point p, and card represents a cardinal number of the set. Thereby, the number of vessel pixel points in the vessel contour corresponding to the third measurement pixel point may be calculated. In some examples, T may be 0.9. Thereby, vessel pixel points and non-vessel pixel points in the vessel contour corresponding to the third measurement pixel may be distinguished. In some examples, the vessel diameter l corresponding to the third measurement pixel point may satisfy $l=n\times s/e$, where n is the number of vessel pixel points in the vessel contour corresponding to the third measurement pixel point, s is a pre-set accuracy, and e is a pre-set multiple. Thus, the vessel diameter may be calculated.

As noted above, the pre-set multiple may be an integer greater than one. The pre-set accuracy may be a decimal greater than zero and less than one. In some examples, different pre-set multiples e and pre-set accuracies s may be used to measure the vessel diameter of the same section of vessel to obtain the measurement result of the vessel diameter with higher precision. In some examples, the results of measurement on the same segment of vessel are shown in Table 1. The mean value is a mean value of vessel diameter, and the standard deviation is a standard deviation of the vessel diameter.

TABLE 1

Partial results of vessel diameter measurement result comparison

| Measurement parameters | Mean value | Standard deviation |
|---|---|---|
| Manual annotation | 6.4094 | 0.421 |
| e = 1, s = 1 | 5.9365 | 0.7319 |
| e = 5, s = 0.5 | 6.4457 | 0.4737 |
| e = 5, s = 0.1 | 6.435 | 0.4723 |
| e = 5, s = 0.05 | 6.4341 | 0.4707 |
| e = 5, s = 0.01 | 6.4345 | 0.471 |
| e = 10, s = 0.5 | 6.5142 | 0.4799 |
| e = 10, s = 0.1 | 6.5078 | 0.4791 |
| e = 10, s = 0.05 | 6.5069 | 0.4787 |
| e = 10, s = 0.01 | 6.507 | 0.4788 |
| e = 15, s = 0.5 | 6.5341 | 0.4757 |
| e = 15, s = 0.1 | 6.5293 | 0.4757 |
| e = 15, s = 0.05 | 6.5288 | 0.4754 |
| e = 15, s = 0.01 | 6.5289 | 0.4755 |

From the comparison of the measurement results of vessel diameter in Table 1, it may be seen that the mean value of manually labeled vessel diameter is 6.4094, and the standard deviation is 0.421. In the absence of super-resolution technique (i.e., e=1, s=1), the measured mean vessel diameter of the present disclosure is 5.9365 with a standard deviation of 0.7319, which is significantly different from the results of manual annotation. When using the super-resolution technique (i.e. AND), the mean value and standard deviation of vessel diameter measurement are close to the results of manual annotation. Specifically, at e=5 and s=0.05, the mean vessel diameter is 6.4341 with a standard deviation of 0.4707, which is comparable to the manually labeled vessel diameter. It may be seen therefrom that the measurement results using the super-resolution technique are closer to the results of manual annotation, indicating that the super-resolution technique effectively improves the accuracy of vessel diameter measurement.

In some examples, arteriovenous cross-indentation features, arteriolar local stenosis feature, and arteriolar general stenosis features may reflect a condition of hypertension. For example, the arteriolar local stenosis features may reflect the recent presence of elevated blood pressure in the patient. As another example, the arteriovenous cross-indentation features and the arteriolar general stenosis features may reflect the patient's long-term sustained increase in blood pressure. The measurement method based on the present disclosure may assist an ophthalmologist in identifying hypertension.

Figure 15:
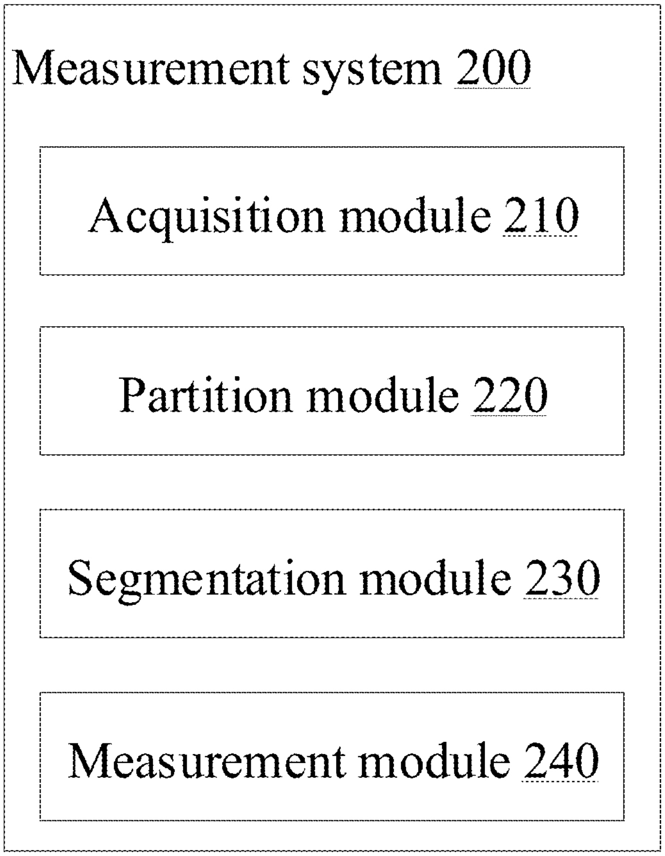
FIG. 15 is a block diagram showing a system for measuring lesion features of hypertensive retinopathy according to an embodiment of the disclosure.

Hereinafter, a lesion feature measurement system 200 (sometimes also referred to simply as a measurement system 200) of hypertensive retinopathy according to the present disclosure will be described in detail with reference to the accompanying drawings. The present disclosure relates to a measurement system 200 for implementing the measurement method described above. FIG. 15 is a block diagram showing a system 200 for measuring lesion features of hypertensive retinopathy according to an embodiment of the disclosure.

As shown in FIG. 15, in some examples, the measurement system 200 may include an acquisition module 210, a partition module 220, a segmentation module 230, and a measurement module 240. The acquisition module 210 may be configured to acquire a fundus image. The partition module 220 may be configured to partition the fundus image to acquire at least three regions. The segmentation module 230 may be configured to perform arteriovenous segmentation on the fundus image to acquire an arteriovenous segmentation result. The measurement module 240 may measure lesion features in the fundus image based on the three regions and the arteriovenous segmentation result. In this case, the lesion features of hypertensive retinopathy in the fundus image may be automatically measured. Thus, the lesion features of hypertensive retinopathy may be measured efficiently and objectively.

In some examples, the acquisition module 210 may be configured to acquire a fundus image. The fundus image may include vessels, which may include arteries and veins. The detailed description may refer to the relevant description in step S110, which will not be repeated here.

In some examples, in the partition module 220, the three regions may include a first region, a second region, and a third region. Thus, three regions may be acquired based on the optic disc region. In some examples, the first region may be a region of a first circle formed by taking a center of a circumscribed circle of the optic disc region as the center and a first pre-set multiple of a diameter of the circumscribed circle as the diameter. In some examples, the first pre-set multiple may be represented by v1. In some examples, v1 may be 1. In some examples, the second region may be a region from the edge of the first region to a second circle formed by taking a center of the circumscribed circle as the center and a second pre-set multiple of the diameter of the circumscribed circle as the diameter. In some examples, the second pre-set multiple may be represented by v2. In some examples, v2 may be 2. In some examples, the third region may be a region from the edge of the second region to a third circle formed by taking a center of the circumscribed circle as the center and a third pre-set multiple of a diameter of the circumscribed circle as the diameter. In some examples, the third pre-set multiple may be represented by v3. In some examples, v3 may be 3. In some examples, let $v1<v2<v3$. The detailed description may refer to the relevant description in step S120, which will not be repeated here.

In some examples, artery and vein segmentation may be performed on the fundus image in the segmentation module 230 by a depth learning-based arteriovenous segmentation model to obtain arteriovenous segmentation results. In some examples, the arteriovenous segmentation model may be trained based on training fundus image and the arteriovenous vessel annotation result. In some examples, the arteriovenous segmentation results may include artery segmentation results and vein segmentation results. In some examples, arteries and veins in the fundus image may be segmented to directly obtain arteriovenous segmentation results. In some examples, the arteriovenous vessel annotation results may include artery annotation results and vein annotation results. In some examples, the arteriovenous vessel annotation results may be formed by annotation vessels in a training fundus image. In some examples, the arteriovenous vessel annotation result may be an artery annotation result and a vein annotation result by annotating a boundary of a vessel with a vessel diameter greater than the pre-set vessel diameter in the training fundus image, and a small vessel annotation result formed by annotating the direction of a small vessel. In some examples, the weight of the region corresponding to the small vessel annotation result may be adjusted based on the small vessel annotation result when calculating the loss function. In this case, annotating a boundary of a larger vessel and the direction of the small vessel in the training fundus image may effectively reduce the difficulty of annotation and the workload, so that the annotation cost may be reduced. In addition, by adjusting the weights of the regions corresponding to the small vessel annotation results, the contribution of the small vessel annotation results with only the direction labeled to the loss function may be controlled, and the accuracy of arteriovenous segmentation may be improved. In some examples, the pre-set vessel diameter may be 50 μm. In some examples, the small vessel may be a vessel that is not greater than the pre-set vessel diameter. In some examples, the weight of the region corresponding to the small vessel annotation result may be adjusted to zero when calculating the loss function. In this case, it is possible to exclude the contribution of the small vessel annotation results with only the direction labeled to the loss function. Thus, it is possible to avoid the influence of the small vessel annotation result having low accuracy in the arteriovenous segmentation on the arteriovenous segmentation model. The detailed description may refer to the relevant description in step S130, which will not be repeated here.

In some examples, the lesion features of hypertensive retinopathy in the fundus image may be measured based on the three regions and the arteriovenous segmentation result. In some examples, the lesion features may include at least one of arteriovenous cross-indentation features, arteriolar local stenosis features, and arteriolar general stenosis features.

In some examples, the arteriovenous cross-indentation features may be measured in the measurement module 240. In some examples, the results of the arteriovenous segmentation of the fundus region except for both the first region and the second region may be refined to obtain the first vessel skeleton. In some examples, the first vessel skeleton may include a plurality of skeleton pixel points as first measurement pixel points. In some examples, the number of skeleton pixel points within a predetermined range of the respective first measurement pixel points may be obtained as a first adjacent point number. In some examples, a pixel point corresponding to a first measurement pixel point having a first adjacent point number greater than a first pre-set number in the arteriovenous segmentation result may be taken as the arteriovenous cross position. In some examples, the artery segmentation results may be expanded such that the expanded artery segmentation result intersects the vein segmentation result to determine the arteriovenous cross position. Thereby, a more accurate arteriovenous cross position may be acquired. In some examples, the arteriovenous cross-indentation features may be measured based on a ratio of the vessel diameters at the proximal and distal ends of the vein segmentation results on both sides of the arteriovenous cross position in the arteriovenous segmentation results. In some examples, the proximal and distal ends on both sides of the arteriovenous cross position may be proximal and distal ends of the arteriovenous division results along the direction of extension of the vein division result and on each of both sides of the arteriovenous cross position. In some examples, if the vein segmentation result is discontinuous at the arteriovenous cross position in the arteriovenous segmentation result, the proximal end of each side may be the skeleton pixel point on the first vessel skeleton of the vein segmentation result which is closest to the arteriovenous cross position. In some examples, if the vein segmentation result in the arteriovenous segmentation results is continuous at the arteriovenous cross position, the proximal end of each side may be the arteriovenous cross position. In some examples, the distal end of each side may be a skeleton pixel point on the first vessel skeleton of the vein segmentation result to which a distance from the arteriovenous cross position is a first pre-set distance. Thus, the proximal and distal ends of both sides of the vein segmentation result may be determined based on the arteriovenous cross position. In some examples, the first pre-set distance may be 2 to 4 times the maximum vessel diameter. In some examples, the first predetermined number may be three. In some examples, the first pre-set distance may be three times the maximum vessel diameter. For detailed description, reference may be made to the relevant description on measuring the arteriovenous cross-indentation features in step S140, and the description thereof will not be repeated here.

In some examples, the arteriolar local stenosis features may be measured in the measurement module 240. In some examples, the artery segmentation results may be refined to obtain a second vessel skeleton. In some examples, the second vessel skeleton may include a plurality of skeleton pixel points as second measurement pixel points. In some examples, the number of skeleton pixel points within a predetermined range of the respective second measurement pixel points may be acquired as the second adjacent point number. In some examples, a second measurement pixel point having a second adjacent point number greater than a second pre-set number may be deleted to obtain a plurality of vessel segments. In some examples, the second predetermined number may be two. In some examples, the arteriolar local stenosis features may be measured based on the ratio of the smallest vessel diameter to the largest vessel diameter for each vessel segment. The detailed description may refer to the relevant description about measuring the arteriolar local stenosis features in step S140, which will not be described here.

In some examples, the arteriolar general stenosis features may be measured in the measurement module 240. In some examples, an artery vessel segment and a vein vessel segment within the third region of the arteriovenous segmentation results may be obtained. In some examples, an arteriole-to-venule ratio may be obtained based on an arterial vessel segment, a vein vessel segment, and a pre-set formula to measure the arteriolar general stenosis features. Thus, the arteriolar general stenosis features may be measured based on the artery vessel segment and the vein vessel segment in the third region. In some examples, the arteriole-to-venule ratio may be a ratio of a central retinal artery equivalent diameter to a central retinal vein equivalent diameter. In some examples, the pre-set formula may be a modified formula of Knudtson. Thus, the arteriolar general stenosis features may be measured based on the modified formula of Knudtson. The detailed description may refer to the relevant description about measuring the arteriolar general stenosis features in step S140, which will not be described here.

In some examples, the measurement system 200 may also include a vessel diameter calculation module (not shown). The vessel diameter calculation module may be used to measure a vessel diameter. In some examples, the arteriovenous segmentation results may be resolution enhanced by a pre-set multiple to generate enhanced arteriovenous segmentation results. In some examples, a vessel skeleton in the enhanced arteriovenous segmentation result may be extracted and fitted to obtain a continuous vessel skeleton and a vessel diameter measurement direction of the third measurement pixel point. In some examples, the third measurement pixel point may be a plurality of pixel points on the continuous vessel skeleton. In some examples, the vessel diameter measurement direction may be perpendicular to a tangent of the continuous vessel skeleton at a third measurement pixel point. In some examples, a vessel contour corresponding to the third measurement pixel point may be generated by an interpolation algorithm and based on the enhanced arteriovenous segmentation result, the third measurement pixel point, the vessel diameter measurement direction of the third measurement pixel point, and the pre-set accuracy. In some examples, the vessel diameter corresponding to the third measurement pixel point may be calculated based on the number of vessel pixel points in the vessel contour corresponding to the third measurement pixel point, the pre-set multiple, and the pre-set accuracy. In this case, the resolution of the vessel in the fundus image may be increased and the vessel diameter may be measured with more pixels. Thus, it is possible to perform automatic super-resolution measurement of the vessel diameter and improve the measurement accuracy of the vessel diameter. In some examples, the vessel diameter 1 corresponding to the third measurement pixel point may satisfy $l=n\times s/e$, where n is the number of vessel pixel points in the vessel contour corresponding to the third measurement pixel point, s is a pre-set accuracy, and e is a pre-set multiple. The detailed description may refer to the relevant description in steps S210 to S240, which will not be repeated here. However, the disclosed examples are not so limited. In other examples, other ways of calculating the vessel diameter may be used.

Although the disclosure has been specifically described above with reference to the accompanying drawings and examples, it should be understood that the above description does not limit the disclosure in any way. Variations and modifications of the disclosure may occur to those skilled in the art as required without departing from the true spirit and scope of the disclosure, and such variations and modifications are intended to fall within the scope of the disclosure Various embodiments of the disclosure may have one or more of the following effects. In some embodiments, the disclosure may provide a method and system for measuring lesion features of hypertensive retinopathy that may efficiently and objectively measure lesion features of hypertensive retinopathy.

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure.

It will be understood that certain features and subcombinations are of utility and may be employed without reference to other features and subcombinations and are contemplated within the scope of the claims. Unless indicated otherwise, not all steps listed in the various figures need be carried out in the specific order described.

What is claimed is:

1. A method for measuring lesion features of hypertensive retinopathy, comprising:

acquiring a fundus image;

identifying an optic disc region of the fundus image and dividing the fundus image into at least three regions comprising a first region, a second region, and a third region based on the optic disc region;

annotating a boundary of a vessel having a vessel diameter greater than a pre-set vessel diameter in a training fundus image to form an artery annotation result and a vein annotation result, and annotating a direction of a vessel having a vessel diameter not greater than the pre-set vessel diameter in the training fundus image to form a small vessel annotation result, thereby obtaining an arteriovenous vessel annotation result comprising the artery annotation result, the vein annotation result, and the small vessel annotation result, wherein the boundary of the vessel is an outer contour of the vessel, the direction of the vessel is an orientation of a centerline of the vessel, and the pre-set vessel diameter is a fixed, predetermined threshold value equal to 50 μm;

training a deep learning-based arteriovenous segmentation model using the training fundus image and the arteriovenous vessel annotation result, comprising adjusting a weight of a region corresponding to the small vessel annotation result based on the small vessel annotation result and calculating a loss function of the arteriovenous segmentation model using the adjusted weight, the adjusted weight controlling a contribution of the region corresponding to the small vessel annotation result to the loss function;

performing artery and vein segmentation on the fundus image by the trained arteriovenous segmentation model to directly acquire an arteriovenous segmentation result comprising an artery segmentation result and a vein segmentation result; and measuring the lesion features of the hypertensive retinopathy in the fundus image based on the three regions and the arteriovenous segmentation results, the lesion features comprising at least one of arteriovenous cross-indentation features, arteriolar local stenosis features, and arteriolar general stenosis features.

2. The measuring method according to claim 1, wherein:

the first region is a region of a first circle formed by taking a circle center of a circumscribed circle of the optic disc region as the center and a first pre-set multiple (v1) of a diameter of the circumscribed circle as the diameter;

the second region is a region from an edge of the first region to a second circle formed by taking the circle center as the center and a second pre-set multiple (v2) of the diameter of the circumscribed circle as the diameter;

the third region is a region from an edge of the second region to a third circle formed by taking the circle center as the center and a third pre-set multiple (v3) of the diameter of the circumscribed circle; and $$v1<v2<v3.$$

3. The measuring method according to claim 2, wherein:

if the arteriovenous cross-indentation features are measured, the arteriovenous segmentation results of a fundus region except the first region and the second region are thinned to acquire a first vessel skeleton comprising a plurality of skeleton pixel points taken as first measurement pixel points and to acquire a number of skeleton pixel points within a pre-set range of each of the first measurement pixel points as a first adjacent point number;

pixel points in the arteriovenous segmentation results correspond to the first measurement pixel points of which the number of first adjacent points is greater than a first pre-set number are taken as arteriovenous cross positions;

arteriovenous cross-indentation features are measured based on a ratio of proximal and distal vessel diameters in the arteriovenous segmentation results along the direction of extension of the vein segmentation result and on each of both sides of the arteriovenous cross position; and the first pre-set number is 3.

4. The measuring method according to claim 3, wherein:

if the vein segmentation result is discontinuous at the arteriovenous cross position in the arteriovenous segmentation result, a proximal end of each side is a skeleton pixel point on the first vessel skeleton of the vein segmentation result which is closest to the arteriovenous cross position;

if the vein segmentation result is continuous at the arteriovenous cross position in the arteriovenous segmentation result, the proximal end of each side is the arteriovenous cross position;

a distal end of each side is a skeleton pixel point on the first vessel skeleton of the vein segmentation result to which a distance from the arteriovenous cross position is a first pre-set distance; and the first pre-set distance is 2 to 4 times of a maximum vessel diameter.

5. The measuring method according to claim 2, wherein:

if the arteriolar local stenosis features are measured, the artery segmentation result is thinned to acquire a second vessel skeleton comprising a plurality of skeleton pixel points taken as second measurement pixel points;

a number of skeleton pixel points within a pre-set range of each of the second measurement pixel points are acquired as a second adjacent point number, the second measurement pixel points with the number of second adjacent points being greater than the second pre-set number are deleted to obtain a plurality of vessel segments; and the arteriolar local stenosis features are measured based on a ratio of a minimum vessel diameter to a maximum vessel diameter of each vessel segment.

6. The measuring method according to claim 5, wherein:

the second pre-set number is 2;

v1 is 1, v2 is 2, and v3 is 3; and the pre-set vessel diameter is 50 μm.

7. The measuring method according to claim 1, wherein the arteriovenous segmentation result is a three-value image.

8. The measuring method according to claim 1, wherein the measurement is performed using the vessels with the diameter larger than the pre-set vessel diameter in the arteriovenous segmentation result.

9. The measuring method according to claim 1, wherein the direction is used to estimate a region corresponding to a vessel not greater than the pre-set vessel diameter and the region is a curve that follows the direction of the vessel not greater than the pre-set vessel diameter.

10. The measuring method according to claim 1, wherein:

measuring a vessel diameter comprises performing resolution enhancement on the arteriovenous segmentation result according to a pre-set multiple to generate an enhanced arteriovenous segmentation result;

extracting a vessel skeleton in the enhanced arteriovenous segmentation result and fitting the vessel skeleton to obtain a vessel diameter measurement direction of a continuous vessel skeleton and third measurement pixel points, the third measurement pixel points being a plurality of pixel points on the continuous vessel skeleton, and the vessel diameter measurement direction being perpendicular to a tangent line of the continuous vessel skeleton at the third measurement pixel points;

using an interpolation algorithm to generate a vessel contour corresponding to the third measurement pixel points based on the enhanced arteriovenous segmentation result, the third measurement pixel points, the vessel diameter measurement direction of the third measurement pixel points, and a pre-set accuracy;

calculating a vessel diameter corresponding to the third measurement pixel points based on a number of vessel pixel points in the vessel contour corresponding to the third measurement pixel points, the pre-set multiple, and the pre-set accuracy; and a vessel diameter/corresponding to the third measurement pixel points satisfies:

$$l=n\times s/e;$$

wherein n is the number of vessel pixel points in the vessel contour corresponding to the third measurement pixel points, s is the pre-set accuracy, and e is the pre-set multiple.

11. The measuring method according to claim 1, wherein the weight is adjusted to zero.

12. The measuring method according to claim 1, wherein the arteriovenous segmentation result further comprises a background segmentation result.

13. The measuring method according to claim 1, wherein the training of the arteriovenous segmentation model further comprises preprocessing the training fundus image and the arteriovenous vessel annotation result to acquire a preprocessed fundus image and a preprocessed arteriovenous vessel annotation result, wherein the arteriovenous segmentation model is trained based on the preprocessed fundus image and the preprocessed arteriovenous vessel annotation result, the preprocessed arteriovenous vessel annotation result is taken as a true value to calculate the loss function, and the arteriovenous segmentation model is optimized by the loss function until a value of the loss function converges to an optimum.

* * * * *